(12) United States Patent
Olivero et al.

(10) Patent No.: US 7,273,886 B2
(45) Date of Patent: *Sep. 25, 2007

(54) BENZOFURAN INHIBITORS OF FACTOR VIIA

(75) Inventors: Alan G. Olivero, Half Moon Bay, CA (US); Daniel P. Sutherlin, So. San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 10/850,231

(22) Filed: May 19, 2004

(65) Prior Publication Data

US 2004/0235852 A1    Nov. 25, 2004

Related U.S. Application Data

(60) Provisional application No. 60/471,879, filed on May 20, 2003.

(51) Int. Cl.
*A61K 31/64* (2006.01)

(52) U.S. Cl. .................. 514/469; 514/470; 549/466; 549/467

(58) Field of Classification Search ............ 549/466, 549/467; 514/469, 470
See application file for complete search history.

(56) References Cited

U.S. PATENT DOCUMENTS

| | | | |
|---|---|---|---|
| 3,282,933 | A | 11/1966 | Nys et al. |
| 5,399,487 | A | 3/1995 | Butenas et al. |
| 5,589,173 | A | 12/1996 | O'Brien et al. |
| 5,646,165 | A | 7/1997 | Abelman et al. |
| 5,656,600 | A | 8/1997 | Abelman et al. |
| 5,656,645 | A | 8/1997 | Tamura et al. |
| 5,658,930 | A | 8/1997 | Tamura et al. |
| 5,658,939 | A | 8/1997 | Abelman et al. |
| 5,670,479 | A | 9/1997 | Abelman et al. |
| 5,998,424 | A | 12/1999 | Galemmo, Jr. et al. |
| 6,020,357 | A | 2/2000 | Pinto et al. |
| 6,034,103 | A | 3/2000 | Buckman et al. |
| 6,034,104 | A | 3/2000 | Klimkowski et al. |
| 6,140,353 | A | 10/2000 | Ackermann et al. |
| 6,358,960 | B1 | 3/2002 | Senokuchi et al. |
| 6,410,536 | B1 | 6/2002 | Dudley et al. |
| 6,472,393 | B1 | 10/2002 | Aliagas-Martin et al. |

FOREIGN PATENT DOCUMENTS

| | | |
|---|---|---|
| DE | 197 18 181 A1 | 11/1998 |
| EP | 0 976 722 | 2/2000 |
| EP | 0 987 274 | 3/2000 |
| WO | WO93/15756 | 8/1993 |
| WO | WO94/13693 | 6/1994 |
| WO | WO96/10022 | 4/1996 |
| WO | WO96/16940 | 6/1996 |
| WO | WO96/40679 | 12/1996 |
| WO | WO97/30073 | 8/1997 |
| WO | WO98/46591 | 10/1998 |
| WO | WO98/46626 | 10/1998 |
| WO | WO98/46627 | 10/1998 |
| WO | WO98/46628 | 10/1998 |
| WO | WO 00/15658 | 3/2000 |
| WO | WO 00/41531 | 7/2000 |
| WO | WO 01/23349 | 4/2001 |
| WO | WO 02/22575 | 3/2002 |
| WO | WO 03/029226 | 4/2003 |

OTHER PUBLICATIONS

Katakura, S. et al., "A novel factor Xa inhibitor: structure-activity relationships and selectivity between factor Xa and thrombin" *Biochem.&Biophys. Res. Comm.* 197:965-972 (1993).

Lam et al., "Structure-Based Design of Novel Guanidine/Benzamidine Mimics: Potent and Orally Bioavailable Factor Xa Inhibitors as Novel Anticoagulants" *J. Med. Chem.* 46:4405-4418 (2003).

Lawson; J.H. et al., "A model for the tissue factor pathway to thrombin" *Journal of Biological Chemistry* 269:23357-23366 (1994).

Renatus et al., "Structural and Functional Analyses of Benzamidine-Based Inhibitors in Complex with Trypsin: Implications for the Inhibition of Factor Xa, tPA, and Urokinase" *J. Med. Chem.* 41:5445-5456 (1998).

*Primary Examiner*—Amelia A. Owens
(74) *Attorney, Agent, or Firm*—Min Wang

(57) ABSTRACT

Compounds of Formula I are useful for inhibiting serine protease enzymes, such as TF/factor VIIa, factor Xa, thrombin and kallikrein and have improved pharmacokinetic properties. These compounds may be used in methods of preventing and/or treating clotting disorders.

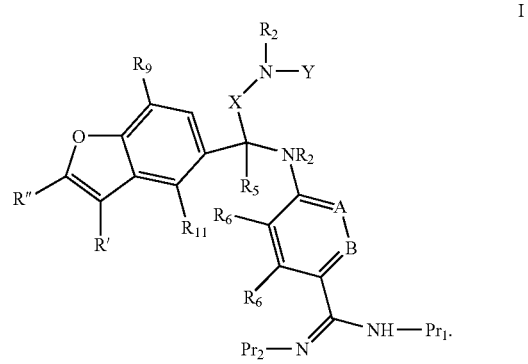

33 Claims, 3 Drawing Sheets

BENZOFURAN INHIBITORS OF FACTOR VIIA

This non-provisional application filed under 37 CFR §1.53(b), claims the benefit under 35 USC § 119(e) of U.S. Provisional Application Ser. No. 60/471,879 filed on May 20, 2003.

FIELD OF THE INVENTION

In one aspect, the invention relates to novel benzofuran compounds which are inhibitors of Tissue Factor (TF)/factor VIIa, factor VIIa, factor Xa, thrombin and/or kallikrein, as well as compositions containing these compounds. The benzofuran compounds are useful for inhibiting these factors and for treating disorders mediated thereby. For example, the compounds are useful for preventing thrombosis or treating abnormal thrombosis in a mammal by inhibiting TF/factor VIIa, factor Xa, thrombin and/or kallikrein.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs.

Many significant disease states are related to abnormal haemeostasis. For example, local thrombus formation due to the rupture of atherosclerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel. Furthermore, a high percentage of patients undergoing surgery, particularly in the lower extremities, suffer thrombus formation in the venous vascular system which results in reduced blood flow to the affected area. Each year in the United States, thromboprophylaxis affects approximately 3.3 million patients and deep vein thrombosis occurs in approximately 600,000 patients. Stroke occurs in approximately 5 million patients each year which have episodic atrial fibrillation. Venous thromboembolism, especially in cancer patients, is another manifestation of thrombus disorder.

There continues to be a need for safe and effective therapeutic anticoagulants to limit or prevent thrombus formation.

Blood coagulation is vital for the containment of bodily fluids upon tissue injury and is an important component of host defense mechanisms. Coagulation or clotting involves the sequential activation of multiple zymogens in a process leading to thrombin generation and the conversion of fibrinogen to an impermeable cross-linked fibrin clot. Thrombin production is the result of a blood coagulation cascade which has been intensively studied and increasingly characterized. See for example, Lawson, J. H., et al. (1994) J. Biol. Chem. 269:23357. The coagulation reactions of this cascade involve initiation, amplification and propagation phases. Additionally, the cascade has been divided into extrinsic and intrinsic pathways. The intrinsic coagulation cascade pathway involves factors XII, XI, and IX and leads to the formation of a complex of factor IXa with its cofactor, factor VIIIa. This complex converts factor X to Xa. Factor Xa is an enzyme which forms a complex with its cofactor, factor Va, and rapidly converts prothrombin to thrombin. Thrombin converts fibrinogen to fibrin monomers which polymerize to form a clot. The extrinsic pathway involves factor VIIa and tissue factor, which form a complex (TF/factor VIIa), and convert factor X to Xa. As in the intrinsic pathway, factor Xa converts prothrombin to thrombin.

Thrombin (factor IIa), as noted above, occupies a central position in the coagulation cascade by converting fibrinogen to fibrin. Consequently, substantial synthetic efforts have been directed to the development of thrombin inhibitors. See, for example, U.S. Pat. Nos. 5,656,600; 5,656,645; 5,670,479; 5,646,165; 5,658,939; 5,658,930 and WO 97/30073. Additional compounds which have been prepared as synthetic thrombin inhibitors are N-arylsulfinated phenylalanine amides.

Approved anticoagulant therapeutics include orally-administered Warfarin (COUMADIN®) and the subcutaneous injectable LMWH (Low Molecular Weight Heparins). Ximelagatran (EXANTA®) is under development (AstraZeneca) as an oral direct thrombin inhibitor for the prevention and treatment of venous thromboembolism (VTE) and for prevention of stroke in patients with atrial fibrillation. Known inhibitors of factor Xa include bisamidine compounds (Katakura, S. (1993) Biochem. Biophys. Res. Commun., 197:965) and compounds based on the structure of arginine (WO 93/15756; WO 94/13693). Phenyl and naphthylsulfonamides have also been shown to be factor Xa inhibitors (WO 96/10022; WO 96/16940; WO 96/40679).

TF/factor VIIa is a serine protease complex that participates in blood coagulation by activating factor X and/or factor IX. Factor VIIa is produced from its precursor, factor VII, which is synthesized in the liver and secreted into the blood where it circulates as a single chain glycopeptide. The cDNA sequence for factor VII has been characterized (Hagen et al. (1986) Proc. Natl. Acad. Sci. U.S.A., 83:2412–2416).

A variety of natural and synthetic inhibitors of TF/factor VIIa are known and have varying potency and selectivity. Tissue factor pathway inhibitor (TFPI; Broze, 1995, Thromb. Haemostas., 74:90) and nematode anticoagulant peptide c2 (NAPc2; Stanssens et al (1996) Proc. Natl. Acad. Sci. U.S.A., 93:2149) bind factor Xa prior to the formation of a quaternary inhibitory complex with the TF/factor VIIa complex. Small protein direct inhibitors (Dennis et al, 1994, J. Biol. Chem., 35:22137) and inactive forms of TF/factor VIIa are also known (Kirchhofer et al (1995) Arteriosclerosis, Thrombosis and Vascular Biol., 15:1098; Jang et al (1995) Circulation, 92:3041). Additionally, synthetic peptides and soluble forms of mutant TF which retain binding affinity but have reduced cofactor activity have been prepared (Roenning et al (1996) Thromb. Res., 82:73; Kelley et al, (1997) Blood, 89:3219). U.S. Pat. No. 5,679,639 describes polypeptides and antibodies which inhibit serine protease activity. U.S. Pat. No. 5,580,560 describes a mutant factor VIIa which has an improved half-life. U.S. Pat. No. 5,504,067 and U.S. Pat. No. 5,504,064 describe a truncated TF for the treatment of bleeding. Kunitz domain-tissue factor fusion proteins have also been shown to be bifunctional anticoagulants (Lee et al (1997) Biochemistry, 36:5607–5611). The TF/factor VIIa complex has been indicated as an attractive target for the development of inhibitors based on a dissociation between surgical bleeding and prevention of intravascular thrombosis (Harker et al (1995) Thromb. Haemostas., 74:464).

Compounds which block or inhibit enzymes in the coagulation cascade are therapeutically useful in treating or preventing thrombosis in a mammal suspected of having a condition characterized by abnormal thrombosis. For example, with respect to arterial vasculature, abnormal thrombus formation due to deterioration of an established atherosclerotic plaque is a major cause of acute myocardial infarction and unstable angina. Treatment of an occlusive coronary thrombus by thrombolytic therapy or percutaneous transluminal coronary angioplasty (PTCA) may be accompanied by reclosure of the vessel. In the venous vasculature, many patients undergoing surgery, particularly in the abdominal and lower body regions, experience thrombus formation which reduces blood flow and can lead to a pulmonary embolism. Disseminated intravascular coagulopathy in both the venous and arterial systems occurs commonly during septic shock, some viral infections, and cancer and may lead to rapid and widespread thrombus formation and organ failure.

Coumarin type, e.g. Warfarin, have certain therapeutic limitations, including excessive bleeding (minor and major hemorrhage. The typically slow onset of action (prothrombic) and long duration of action also complicate emergency procedures and necessitates frequent monitoring (Levine et al (1995) Chest 108 (4S), 276S; Lafata et al (2000) Thrombosis and Thrombolytics 9:S13; Marchetti et al (2001) Am. J. Med. 111:130; Garcia-Zozaya, I. (1998) J. of Kent. Med. Assoc. 96(4):143). Also, typically the cost of monitoring blood levels far exceeds the cost of coumarin and heparin type anticoagulant therapy.

PTCA and recanalization are favored procedures for treating occluded vessels. However, arterial thrombosis following these procedures remains a leading cause of failure. Heparin, the most widely used anticoagulant, has not been shown to be entirely effective in the treatment and prevention of acute arterial thrombosis or rethrombosis.

The synthesis and development of small molecule inhibitors based on the known three-dimensional structure of proteins is a challenge of modem drug development. Many thrombin inhibitors have been designed to have a hirudin-type structure. Stubbs and Bode, *Current Opinion in Structural Biology* 1994, 4:823–832. New synthetic thrombin inhibitors, as well as inhibitors of factor Xa and TF/factor VIIa, are reported. See, for example, *Annual Reports in Medicinal Chemistry*, 1995–1997, Academic Press, San Diego, Calif.; U.S. Pat. No. 5,589,173 and U.S. Pat. No. 5,399,487.

U.S. Pat. No. 6,472,393 and WO 00/41531 describe a class of inhibitors of serine proteases such as TF/factor VIIa, and which have acylsulfonamide and benzamidine moieties. These serine protease inhibitors have proven to have potent antithrombotic activity in vivo. However, there remains a need for potent TF/factor VIIa inhibitors that have optimized activity, selectivity and pharmacokinetic properties such as clearance, half life and bioavailability. Prodrug forms of TF/factor VIIa inhibitors may be employed to establish improved oral bioavailability.

SUMMARY OF THE INVENTION

An aspect of the present invention is novel compounds which inhibit factors/enzymes in the coagulation cascade and which are useful to prevent or treat thrombus formation in arterial or venous vessels. These compounds are useful as coagulation factor inhibitors and as anticoagulants in general.

In one embodiment, the compounds of the invention selectively inhibit TF/factor VIIa, Xa, or kallikrein.

One aspect of the invention is to provide methods of inhibiting TF/factor VIIa, Xa or thrombin activity by contacting these enzymes with an effective inhibitory amount of the novel inhibitors of the present invention or a composition containing these compounds. A further object is to provide a method of treating a TF/factor VIIa, Xa or thrombin mediated disorder by administering to a mammal in need of such treatment an effective amount of one of the compounds of the invention or a composition containing the compound. An additional object is to provide a method of preventing thrombosis or treating abnormal thrombosis by administering to a mammal in need of such treatment an effective amount of one of the compounds of the invention or a composition containing the compound and a carrier or excipient.

The present invention provides novel compounds with biological activity against thromboembolic and coagulation disorders. The benzofuran compounds of the invention may be useful for treating human patients with such disorders.

In an aspect of the invention there is provided benzofuran compounds having the general formula I

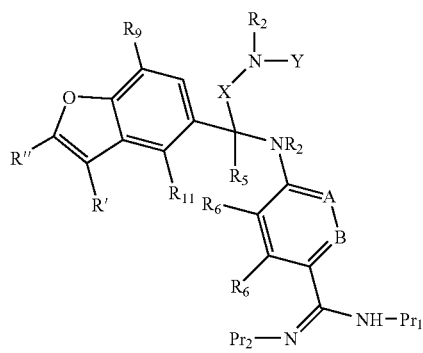

wherein
A and B are independently CH, $CR_3$ or N;
X is C=O or $(CR_{4a}R_{4b})_m$ where m=1 or 2;
Y is $S(O)_n$—$R_1$, $S(O)_n$—$NR_2R_2$, $S(O)_n$—$OR_2$, $C(O)R_1$, $C(S)R_1$, $C(O)$—$OR_1$, or $C(O)$—$NR_2R_2$, where n is 1 or 2;
$Pr_1$ and $Pr_2$ are independently H, hydroxy, alkyl, alkoxy, alkanoyl, alkanoyloxy, alkoxycarbonyl, aryloxy, or arylalkoxy;
said alkyl, alkoxy, alkanoyl, alkanoyloxy, alkoxycarbonyl, aryloxy or arylalkoxy are independently and optionally substituted with hydroxy, halogen, carboxyl, alkyl, halosubstituted alkyl, alkoxy, a carbocycle or a heterocycle;
said carbocycle and heterocycle are optionally substituted with 1–5 hydroxy, alkoxy, carboxyl, alkyl, or halosubstituted alkyl; and
one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—;
R' and R" are each independently H, carboxyl, alkyl, alkoxy, alkanoyl, alkanoyloxy or alkoxycarbonyl; wherein said alkyl, alkoxy, alkanoyl, alkanoyloxy and alkoxycarbonyl groups are optionally substituted with amino, hydroxy, alkoxy, acyl, acyloxy, a substituted or unsubstituted carbocycle or heterocycle; and one to three carbon atoms of said alkyl, alkoxy alkanoyl, alkanoyloxy or alkoxycarbonyl chain are optionally replaced with O, C(O), NH, S, $SO_2$, —OC(O)—, C(O)O— or —OC(O)NH—;
$R_1$ is $C_1$–$C_6$ alkyl, $C_2$–$C_6$ alkenyl, $C_2$–$C_6$ alkynyl, $C_3$–$C_6$ cycloalkyl, phenyl, naphthyl, benzyl or heteroaryl;
each $R_2$ is, independently, H, alkyl, substituted alkyl, aryl, substituted aryl, $C(O)R_7$ or $C(NH)R_7$, or the two $NR_2$ and NR$_2$ groups together form a heterocycle, for example, to form an imide group N—C(O)—N;

R$_3$ is H, C$_1$–C$_6$ alkyl, C$_1$–C$_6$ alkoxy, halogen or OH;

R$_{4a}$ and R$_5$ are independently a member selected from the group consisting of H, unsubstituted or substituted alkyl, unsubstituted or substituted alkoxyalkyl, unsubstituted or substituted haloalkyl, unsubstituted or substituted aryl, alkyl-OR$_7$, alkyl-NR$_7$R$_8$, alkyl-OC(O)R$_7$, alkyl-C(O)OR$_7$, alkyl-C(O)R$_7$, OC(O)R$_7$, C(O)OR$_7$, C(O)R$_7$ and members in which the alkyl, R$_7$ or R$_8$ is substituted with 1–3 F, Cl, Br, I, OR$_7$, SR$_7$, NR$_7$R$_8$, OC(OR$_7$), C(O)OR$_7$, C(O)R$_7$, C(O)NR$_7$R$_8$, NHC(NH)NH$_2$, PO$_3$, unsubstituted or substituted indolyl or unsubstituted or substituted imidazolyl groups;

R$_{4b}$ is H, alkyl, or substituted alkyl;

R$_6$ is selected from the group selected from H, C$_1$–C$_6$ alkyl, C$_1$–C$_6$ alkyl-OR$_7$, C$_1$–C$_6$ alkyl-NR$_7$R$_8$, C$_1$–C$_6$ haloalkyl, halo, cyano, OR$_7$, SR$_7$, NR$_7$R$_8$, C(O)OR$_7$, C(O)R$_7$ and OC(O)R$_7$;

R$_7$ and R$_8$ are independently H or C$_1$–C$_6$ alkyl;

R$_9$ is H, halogen, hydroxy, alkyl, alkoxy, alkanoyl, NR$_7$R$_8$ or SR$_7$; wherein said alkyl, alkoxy, and alkanoyl are optionally substituted with halogen, amino, hydroxy, carboxyl, alkoxy or alkoxycarbonyl;

R$_{11}$ is selected from the group consisting of H, halo, nitro, cyano, C$_1$–C$_6$ alkyl, C$_6$–C$_{10}$ aryl, NR$_7$R$_8$, OR$_7$, SR$_7$, C$_1$–C$_6$ alkyl-C(O)R$_7$, C$_1$–C$_6$ alkyl-C(O)NR$_7$R$_8$, C$_1$–C$_6$ alkyl-C(O)OR$_7$, C$_1$–C$_6$ alkyl-OC(O)R$_7$, C$_1$–C$_6$ alkyl-OR$_7$, OC$_1$–C$_6$ alkyl-C(O)R$_7$, OC$_1$–C$_6$ alkyl-C(O)OR$_7$, OC$_1$–C$_6$ alkyl-OC(O)R$_7$, O—C$_1$–C$_6$ alkyl-OR$_7$, OC$_1$–C$_6$ alkyl-C(O)NR$_7$R$_8$, C$_1$–C$_6$ haloalkyl, OR$_{12}$, C$_1$–C$_6$ alkyl-R$_{12}$, O—C$_1$–C$_6$ alkyl-R$_{12}$, C(O)OR$_7$, C(O)OR$_{12}$, C(O)NR$_7$R$_8$, OC(O)NR$_7$R$_8$, NR$_7$C(O)R$_7$, NR$_7$C(O)R$_{12}$, NR$_7$C(O)—NR$_7$R$_8$, NR$_7$—(C$_1$–C$_6$ alkyl)-C(O)—NR$_7$R$_8$, NR$_7$C(O)OR$_7$, NR$_7$C(O)OR$_{12}$, NR$_7$S(O)$_n$—R$_1$, NR$_7$S(O)$_n$—R$_7$ and NR$_7$S(O)$_n$—R$_{12}$, wherein R$_{12}$ is unsubstituted or substituted C$_6$–C$_{10}$ aryl or heterocycle and n is 1 or 2; and acid and base addition salts and prodrugs thereof.

Prodrug forms of Formula I compounds, e.g. where acetamidine substituents Pr$_1$ and/or Pr$_2$ forms a prodrug moiety, may possess improved pharmacokinetic, e.g. oral bioavailability, properties.

Another aspect of the invention is a pharmaceutical formulation including a Formula I compound, or a pharmaceutically acceptable salt or solvate thereof, and a pharmaceutically acceptable diluent, carrier, or excipient.

One aspect of the invention provides novel, orally available anticoagulant pharmaceutical formulations of the compounds of the invention with improved properties.

Another aspect of the invention provides a pharmaceutical combination comprising an effective amount of a Formula I compound and a second compound having therapeutic properties.

In another aspect of the invention there is provided methods of inhibiting TF/factor VIIa, factor Xa, thrombin or kallikrein activity, comprising contacting TF/factor VIIa, factor Xa, thrombin or kallikrein with an effective amount of a compound of formula I.

In another aspect of the invention there is provided methods of treating a TF/factor VIIa, factor Xa, thrombin or kallikrein mediated disorder, comprising administering to a mammal in need thereof an effective amount of a benzofuran compound of Formula I.

Another aspect of the invention includes articles of manufacture, i.e. kits, comprising benzofuran compound of Formula I, a container, and a package insert or label indicating a treatment.

Another aspect of the invention includes methods of preparing, methods of synthesis, methods of separation, and methods of purification of the benzofuran compound of Formula I.

DETAILED DESCRIPTION OF THE INVENTION

Definitions

Figure 1:
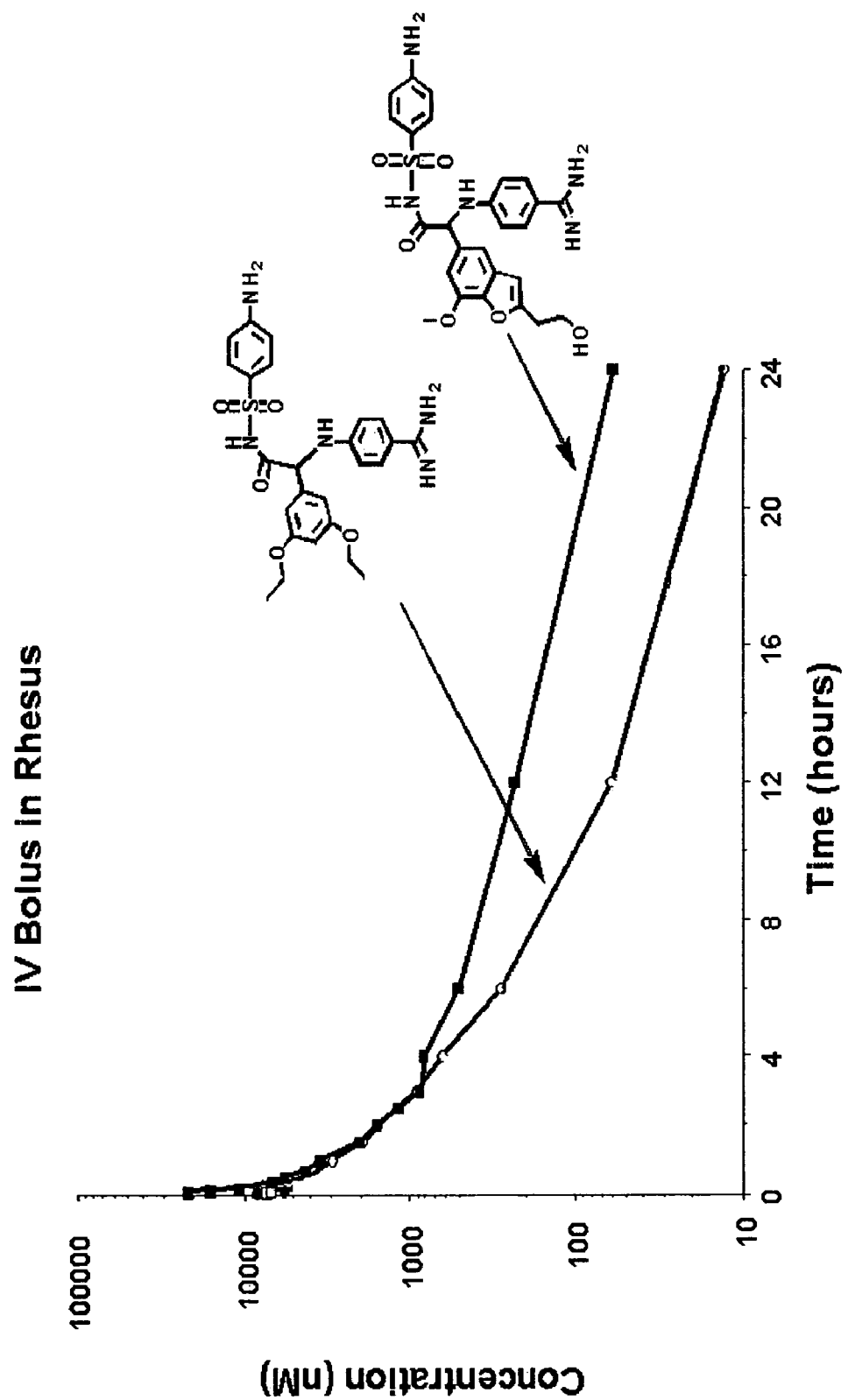
FIG. 1 shows a graph of plasma concentrations of a benzofuran, p-aminophenyl sulfonamide VIIa inhibitor and a 3,5 bis-ethoxyphenyl, p-aminophenyl sulfonamide VIIa inhibitor following IV bolus administration in rhesus monkey.

The terms "factor VIIa", "TF/factor VIIa", "Tissue factor VIIa", "factor Xa", "thrombin" or "kallikrein" relating to a disorder mean a disease or physiological condition involving clotting of the blood and in which inhibition of one or more of these enzymes reduces or eliminates at least one of the physiological symptoms of the disease or condition.

The term "thrombosis" means the development of or formation of a blood clot or thrombus in a blood vessel of a mammal or in a synthetic vessel, such as a plastic or glass tube or vial. A thrombus which has detached from its original site and is found in another site is called a thrombotic embolus.

The term "abnormal thrombosis" means thrombosis occurring in a mammal which is contrary to the good health of the mammal.

The term "alkyl", used alone or as part of another term, means a branched or unbranched, saturated aliphatic hydrocarbon group, having the number of carbon atoms specified, or if no number is specified, having up to and including 12 carbon atoms, represented as C$_n$–C$_m$ alkyl, or where n and m are specified as integers. Examples of alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "C$_1$–C$_6$ alkyl" and "alkyl of 1 to 6 carbon atoms" are synonymous and used interchangeably. Exemplary "C$_1$–C$_6$ alkyl" groups are methyl, ethyl, 1-propyl, isopropyl, 1-butyl or sec-butyl.

The terms "substituted alkyl" or "substituted C$_n$–C$_m$ alkyl" where m and n are integers identifying the range of carbon atoms contained in the alkyl group, denotes the above alkyl groups that are substituted by one, two or three halogen (F, Cl, Br, I), trifluoromethyl, hydroxy, unsubstituted and substituted C$_1$–C$_7$ alkoxy, protected hydroxy, amino (including alkyl and dialkyl amino), protected amino, unsubstituted and substituted C$_1$–C$_7$ acyloxy, unsubstituted and substituted C$_3$–C$_7$ heterocyclic, unsubstituted and substituted phenoxy, nitro, carboxyl, protected carboxyl, unsubstituted and substituted carboalkoxy, unsubstituted and substituted acyl, carbamoyl, carbamoyloxy, cyano, methylsulfonylamino, unsubstituted and substituted benzyloxy, unsubstituted and substituted $C_3$–$C_6$ carbocyclyl or $C_1$–$C_4$ alkoxy groups. The substituted alkyl groups may be substituted once, twice or three times with the same or with different substituents.

Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, trifluoroethyl, trifluoropropyl, carboxypropyl, 2-aminopropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocyclo group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. An exemplary subgroup within the above group includes the substituted methyl group, e.g. a methyl group substituted by the same substituents as the "substituted $C_n$–$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

The term "alkoxy" denotes groups having the number of carbon atoms specified such as methoxy, ethoxy, n-propoxy, isopropoxy, n-butoxy, s-butoxy, t-butoxy and like groups. The term "substituted alkoxy" means these alkoxy groups substituted by the same substituents as the "substituted $C_n$–$C_m$ alkyl" group, for example, 2,2,2-trifluoroethoxy, 2,2,2-trifluoropropoxy, etc.

The term "acyloxy" denotes herein carboacyloxy groups having the specified number of carbon atoms such as formyloxy, acetoxy, propionyloxy, butyryloxy, pentanoyloxy, hexanoyloxy, heptanoyloxy, and the like. The term "substituted acyloxy" means these acyloxy groups substituted by the same substituents as the "substituted $C_n$–$C_m$ alkyl" group.

The term "alkylcarbonyl", "alkanoyl" and "acyl" are used interchangeably herein encompass groups having the specified number of carbon atoms such as formyl, acetyl, propionyl, butyryl, pentanoyl, hexanoyl, heptanoyl, benzoyl and the like.

The terms "carbocyclyl", "carbocyclylic" and "carbocyclo" alone and when used as a moiety in a complex group such as a carbocycloalkyl group, refers to a mono-, bi-, or tricyclic aliphatic ring having 3 to 14 carbon atoms, e.g. 3 to 7 carbon atoms. Exemplary carbocyclic groups include cyclopropyl, cyclobutyl, cyclopentyl and cyclohexyl groups. The terms "substituted carbocyclyl" and "carbocyclo" mean these groups substituted by the same substituents as the "substituted $C_n$–$C_m$ alkyl" group.

A "carbocycloalkyl" group is a carbocyclo group as defined above covalently bonded to an alkyl group as defined above.

The term "alkenyl" means a branched or unbranched hydrocarbon group having the number of carbon atoms designated containing one or more carbon-carbon double bonds, each double bond being independently cis, trans, or a nongeometric isomer. The term "substituted alkenyl" means these alkenyl groups substituted by the same substituents as the "substituted $C_n$–$C_m$ alkyl" group.

The term "alkynyl" means a branched or unbranched hydrocarbon group having the number of carbon atoms designated containing one or more carbon-carbon triple bonds. The term "substituted alkynyl" means these alkynyl groups substituted by the same substituents as the "substituted $C_n$–$C_m$ alkyl" group.

The terms "alkylthio" and "$C_1$–$C_{12}$ substituted alkylthio" denote $C_1$–$C_{12}$ alkyl and $C_1$–$C_{12}$ substituted alkyl groups, respectively, attached to a sulfur which is in turn the point of attachment for the alkylthio or substituted alkylthio group to the group or substituent designated.

The term "aryl" when used alone or as part of another term means a homocyclic aromatic group whether or not fused having the number of carbon atoms designated or if no number is designated, up to 14 carbon atoms. Aryl groups, "Ar", include phenyl, naphthyl, biphenyl, phenanthrenyl, naphthacenyl, and the like (see e.g. *Lang's Handbook of Chemistry* (Dean, J. A., ed) 13th ed. Table 7-2 [1985]).

The term "aryloxy" denotes a group which comprises an aryl group and an oxygen atom. Aryloxy groups may be represented as ArO—. Examples of aryloxy include phenoxy (($C_6H_5O$—, PhO—)

The term "arylalkoxy" denotes a group which comprises an aryl group, an alkyl group and an oxygen atom Arylalkoxy groups may be represented as Ar—($C_n$–$C_m$ alkyl)-O—. Examples of arylalkoxy include benzyloxy ($C_6H_5CH_2O$—, BnO—).

The term "substituted phenyl" or "substituted aryl" denotes a phenyl group or aryl group substituted with one, two, three, four or five, e.g. 1-2,1-3 or 1-4 substituents chosen from halogen (F, Cl, Br, I), hydroxy, protected hydroxy, cyano, nitro, alkyl (e.g. $C_1$–$C_6$ alkyl), alkoxy (e.g. $C_1$–$C_6$ alkoxy), benzyloxy, carboxyl, protected carboxyl, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclic, aryl, or other groups specified. One or methyne (CH) and/or methylene ($CH_2$) groups in these substituents may in turn be substituted with a similar group as those denoted above. Examples of the term "substituted phenyl" includes but is not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di($C_1$–$C_6$ alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3,4-diethoxyphenyl, 3-ethoxy-4-isopropoxyphenyl, 3-ethoxy-s-butoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl) phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where 1, 2, or 3 of the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Exemplary substituted phenyl groups include the 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Also, the term "substituted phenyl" represents phenyl groups having an aryl, phenyl or heteroaryl group fused thereto. The fused ring may also be substituted with any of the substituents identified above for "substituted alkyl" groups.

The term "aralkyl" means one, two, or three aryl groups having the number of carbon atoms designated, appended to an alkyl group having the number of carbon atoms designated including but not limited to; benzyl ($C_6H_5CH_2$—, Bn-), napthylmethyl, phenethyl ($C_6H_5CH_2CH_2$—), benzhydryl (diphenylmethyl), trityl, and the like. One exemplary arylalkyl group is the benzyl group. Aralkyl groups may be represented as Ar—($C_n$–$C_m$ alkyl)-.

The term "substituted aralkyl" denotes an alkyl group, e.g. $C_1$–$C_8$ alkyl group, substituted at any carbon with an aryl group, e.g. $C_6$–$C_{10}$ aryl group, bonded to the alkyl group through any aryl ring position and substituted on the alkyl portion with one, two or three groups chosen from halogen (F, Cl, Br, I), hydroxy, protected hydroxy, amino, protected amino, $C_1$–$C_7$acyloxy, nitro, carboxyl, protected carboxyl, carbamoyl, carbamoyloxy, cyano, $C_1$–$C_6$ alkylthio, N-(methylsulfonylamino) or $C_1$–$C_4$alkoxy. Optionally the aryl group may be substituted with one, two, three, four or five groups chosen from halogen, hydroxy, protected hydroxy, nitro, $C_1$–$C_6$ alkyl, $C_1$–$C_6$ alkoxy, carboxyl, protected carboxyl, carboxymethyl, protected carboxymethyl, hydroxymethyl, protected hydroxymethyl, aminomethyl, protected aminomethyl, or an N-(methylsulfonylamino) group. As before, when either the $C_1$–$C_8$ alkyl portion or the aryl portion or both are disubstituted, the substituents can be the same or different. This group may also appear as the substituted aralkyl moiety of a substituted aralkoxy group.

Examples of the term "substituted aralkyl" and this group when it occurs in a "substituted aralkoxy" group include groups such as 2-phenyl-1-chloroethyl, 1-phenyl-1-chloromethyl, 1-phenyl-1-bromomethyl, 2-(4-methoxyphenyl) ethyl, 2,6-dihydroxy-4-phenyl(n-hexyl), 5-cyano-3-methoxy-2-phenyl(n-pentyl), 3-(2,6-dimethylphenyl)$_n$-propyl, 4-chloro-3-aminobenzyl, 6-(4-methoxyphenyl)-3-carboxy (n-hexyl), 5-(4-aminomethyl phenyl)-3-(aminomethyl)(n-pentyl), and the like.

The term "carboxyl-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as methyl, ethyl, isopropyl, t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxyl-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Exemplary carboxylic acid protecting groups are the allyl and p-nitrobenzyl groups. Similar carboxyl-protecting groups used in the cephalosporin, penicillin and peptide arts can also be used to protect a carboxyl group substituents. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxyl" refers to a carboxyl group substituted with one of the above carboxy-protecting groups.

As used herein the term "amide-protecting group" refers to any group typically used in the peptide art for protecting the peptide nitrogens from undesirable side reactions. Such groups include p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of these protecting groups can be found in "Protective Groups in Organic Synthesis", by Theodora W. Greene, 1981, John Wiley and Sons, New York.

The terms "heterocyclic group", "heterocyclic", "heterocyclyl", or "heterocyclo" alone and when used as a moiety in a complex group such as a heterocycloalkyl group, are used interchangeably and refer to any mono-, bi-, or tricyclic saturated or non-aromatically unsaturated ring having the number of atoms designated, generally from 3 to about 10 ring atoms, where the ring atoms are carbon and 1,2, 3 or 4 nitrogen, sulfur or oxygen atoms. Typically, a 5-membered ring has 0 to 2 double bonds and 6- or 7-membered ring has 0 to 3 double bonds and the nitrogen or sulfur heteroatoms may optionally be oxidized, and any nitrogen heteroatom may optionally be quaternized. Examples include pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperidinyl, and 3,4,5,6-tetrahydropiperidinyl.

A "heterocycloalkyl" or a "heterocycloalkenyl" group is a heterocyclo group as defined above covalently bonded to an alkyl or alkenyl group as defined above.

Unless otherwise specified, "heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur. For example, at least one heteroatom is nitrogen (*Lang's Handbook of Chemistry*, supra). Included in the definition are any bicyclic groups where any of the above heteroaryl rings are fused to a benzene ring.

The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl.

Heterocyclic 5-membered ring systems containing a sulfur or oxygen atom and one to three nitrogen atoms are also suitable for use in the instant invention. Examples of such groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, e.g. oxazol-2-yl, and oxadiazolyl, such as 1,3,4-oxadiazol-5-yl, and 1,2,4-oxadiazol-5-yl. Further examples of 5-membered ring systems with 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Examples of benzo-fused derivatives are benzoxazol-2-yl, benzthiazol-2-yl and benzimidazol-2-yl.

Further suitable specific examples of the above heterocyclic ring systems are 6-membered ring systems containing one to three nitrogen atoms. Such examples include pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are an exemplary group.

The substituents for the optionally substituted heterocyclic ring systems, and further examples of the 5- and 6-membered ring systems discussed above can be found in Druckheimer et al., U.S. Pat. No. 4,278,793.

"Heteroaryl" includes; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

A "heteroaralkyl" or a "heteroaralkenyl" group is a heteroaryl group as defined above covalently bonded to an alkyl group or to an alkenyl group as defined above.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, trimethamine, dicyclohexylamine, choline, and caffeine.

The term "prodrug" as used herein means a derivative of a parent drug molecule that enhances pharmaceutically desirable characteristics or properties (e.g. transport, bioavailability, pharmacodynamics, etc.) and that requires biotransformation, either spontaneous or enzymatic, within the organism to release the active parent drug.

Embodiments

The invention provides compounds which inhibit factor VIIa and exhibit unexpected and improved pharmacokinetic properties. Compounds of the invention have improved clearance and/or half life in vivo.

In an embodiment of the invention there is provided compounds which specifically inhibit TF/factor VIIa, relative to the inhibition of factor Xa, thrombin or kallikrein.

Another embodiment provides a method of inhibiting TF/factor VIIa, Xa or thrombin activity by contacting these enzymes with an effective inhibitory amount of the novel inhibitors of the present invention or a composition containing these compounds. A further object is to provide a method of treating a TF/factor VIIa mediated disorder by administering to a mammal in need of such treatment an effective amount of one of the compounds of the invention or a composition containing the compound. An additional object is to provide a method of preventing thrombosis or treating abnormal thrombosis by administering to a mammal in need of such treatment an effective amount of one of the compounds of the invention or a composition containing the compound and a diluent, carrier or excipient.

The invention is generally directed to compounds having Formula I which exhibit superior pharmacokinetic properties such as in vivo clearance and/or half life:

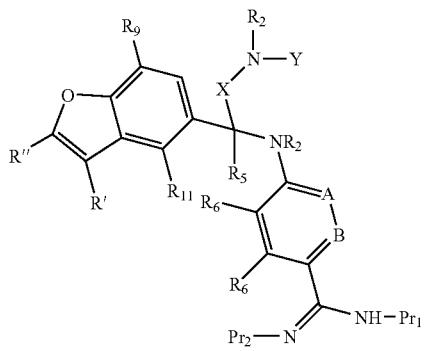

I wherein $R_2$, $R_5$, $R_6$, $R_9$, $R_{11}$ R', R", $Pr_1$, $Pr_2$, A, B, X, and Y have the meanings described above. In these meanings, alkyl includes unsubstituted or substituted $C_1$–$C_6$ alkyl; alkenyl includes unsubstituted or substituted $C_2$–$C_6$ alkenyl; alkynyl includes unsubstituted or substituted $C_2$–$C_6$ alkynyl; aryl includes unsubstituted or substituted naphthyl or phenyl; and aralkyl includes unsubstituted or substituted benzyl.

X is C=O or $(CR_{4a}R_{4b})_m$ wherein m=1 or 2 and $R_{4a}$ and $R_{4b}$ are as described below. In one embodiment X is —$CH_2$—. In another embodiment, X is C(O).

The group Y may be $S(O)_n$—$R_1$ where n=1 or 2 or the group $S(O)_n$—$NR_2R_2$ where n=1 or 2, such as where n is 2 and Y is $S(O)_n$—$R_1$. Y may also be $S(O)_n$—$NR_2R_2$ and n is 2. In another embodiment, X is C(O) and Y is $S(O)_n$—$R_1$ or $S(O)_n$—$NR_2R_2$ thereby forming an acylsulfonamide or acylsulfamide respectively.

In another embodiment, when Y is $S(O)_n$—$R_1$, $R_1$ is selected from the group consisting of $C_1$–$C_6$ alkyl, $C_2$–$C_6$ alkenyl, $C_2$–$C_6$ alkynyl, $C_3$–$C_6$ cycloalkyl, phenyl, naphthyl, benzyl and heteroaryl having 5–6 ring atoms selected from carbon atoms and 1–2 heteroatoms, where the heteroatoms are N, S, or O, and $R_1$ optionally substituted with 1–3 substituents selected from the group consisting of halo, nitro, $C_1$–$C_6$ alkyl, $NR_7R_8$, $OR_7$, $SR_7$, $C_1$–$C_6$ alkyl-C(O) $OR_7$, $C_1$–$C_6$ alkyl-OC(O)$R_7$, $C_1$–$C_6$ alkyl-C(O)$R_7$, $C_1$–$C_6$ alkyl-$OR_7$, $C_1$–$C_6$ haloalkyl, $C_1$–$C_6$ alkyl-$NR_7R_8$, C(O)$OR_7$, OC(O)$R_7$, C(O)$NR_7R_8$, OC(O)$NR_7R_8$, NHC(O)$R_7$, and NHC(O)$NR_7R_8$, where $R_7$ and $R_8$ independently are H or $C_1$–$C_6$ alkyl. In this embodiment, each of the remaining variables $R_2$, $R_5$, $R_6$, $R_9$, $R_{11}$, $Pr_1$, $Pr_2$, R', R", A, B, X and Y may be independently selected to be any of the groups in the respective definitions described above.

In another embodiment, $Pr_1$ and $Pr_2$ are independently a prodrug group which enhances the permeability of the compound and therefore bioavailability and is cleaved upon uptake to provide a free amidine group. $Pr_1$ and $Pr_2$ are independently H, hydroxy, alkyl, alkoxy, alkanoyl, alkanoyloxy, alkoxycarbonyl, aryloxy or arylalkoxy. Said alkyl, alkoxy, alkanoyl, alkanoyloxy, alkoxycarbonyl, aryloxy or arylalkoxy are independently and optionally substituted with hydroxy, halogen, carboxyl, alkyl, halosubstituted alkyl, alkoxy, a carbocycle or a heterocycle. Said carbocycle and heterocycle are optionally substituted with 1–5 hydroxy, alkoxy, carboxyl, alky, or halosubstituted alkyl. One to three carbon atoms of said alkyl, alkoxy alkanoyl, alkanoyloxy or alkoxycarbonyl are optionally replaced with O, C(O), NH, S, $SO_2$, —OC(O)—, C(O)O— or —OC(O)NH—. By "replace" is meant that a carbon atom and pending hydrogen atoms (e.g. a methylene group) of the aliphatic portion of an alkyl, alkoxy, alkanoyl etc. group is substituted with one of the specified atoms or divalent groups. For example, substituting a methylene group for an oxygen atom in an alkyl chain forms an ether. In one embodiment $Pr_2$ is H while $Pr_1$ is selected from the specified groups, such as benzyloxy ($OCH_2Ph$). In another embodiment $Pr_1$ is hydroxy or alkoxy, or alkanoyl optionally substituted with halogen, such as Cl, or tri-substituted with F. In other embodiments, $Pr_1$ is 2-trichloroethyloxycarbonyl, hydroxy or ethoxy. In another embodiment, $Pr_1$ incorporates a carbocycle selected from the group consisting of aryloxy, arylcarbonyl, arylcarbonyloxy, arylalkoxy, arylalkoxycarbonyl, arylalkanoyl or arylalkanoyloxy. $Pr_1$ groups of this type include benzoyl, benzoyl substituted with 1 or 2 $CF_3$ groups, benzoyloxy substituted with 1 or 2 $CF_3$ groups. $Pr_1$ may be phenoxy, benzyloxy, benzyloxy substituted with groups at the ortho, meta, or para positions of the phenyl ring. $Pr_1$ may be benzoyl substituted at both meta positions with $CF_3$ (i.e. 3,5-disubstituted), benzoyl substituted at both a meta and para position with $CF_3$ (i.e. 3,4,-disubstituted) benzoyl substituted at both an ortho and meta position (i.e. 2,3-disubstituted), or benzyloxycarbonyl substituted with $CF_3$ (2,3–3,4- or 3,5-disubstituted). Alternatively, $Pr_1$ is H while $Pr_2$ is selected from one of the specified groups. In such an embodiment $Pr_2$ is alkoxy, such as methoxy, ethoxy, or allyloxy.

R' and R" are each independently H, carboxyl, alkyl, alkoxy, alkanoyl, alkanoyloxy or alkoxycarbonyl; wherein said alkyl, alkoxy, alkanoyl, alkanoyloxy and alkoxycarbonyl groups are optionally substituted with amino, hydroxy, alkoxy, acyl, acyloxy, a substituted or unsubstituted carbocycle or heterocycle; and one to three carbon atoms of said alkyl, alkoxy alkanoyl, alkanoyloxy or alkoxycarbonyl chain are optionally replaced with O, C(O), NH, S, $SO_2$, —OC(O)—, C(O)O— or —OC(O)NH—.

In one embodiment R' is H, halogen alkyl, alkoxy, halo, nitro, cyano, wherein said alkyl and alkoxy are optionally substituted with hydroxy, halogen, alkoxy, aryl and aryloxy. In another embodiment R' is Cl, methyl, ethyl, propyl, hydroxyethyl, benzyloxyethyl. In another embodiment R' is methyl, and $R_{11}$ is H.

In another embodiment R" is alkyl, optionally substituted with amino, hydroxy, alkoxy, acyl, acyloxy, a carbocycle or heterocycle; alkanoyl, alkoxycarbonyloxyalkyl, alkanoyloxyalkyl, acyloxyalkyl or a heterocycle (optionally substituted with halogen, haloalkyl, hydroxy, alkoxy or carboxyl). In one embodiment R" is H, ethyl, propyl, t-butyl, hydroxymethyl, hydroxyethyl, 1-methoxy-1-methylethyl, 1-hydroxy-1-methylethyl, methoxymethyl, aminomethyl, N-dimethylaminomethyl, N-acetylaminomethyl, N-acetyl-N-methylaminomethyl, acetylethyl, propanoyl, acetyl, ethyloxycarbonyloxyemethyl, acetyloxyethyl, t-butylcarbonyloxyethyl, benzoyloxyethyl, 3,5-diCF$_3$-benzoyloxyethyl, trichloroacetyloxyethyl, propanoyloxyethyl, N-morpholino or imidizole-1-yl. In one embodiment R" is H, hydroxymethyl, hydroxyethyl, or propyl.

$R_9$ is H, halogen, hydroxy, alkyl, alkoxy, alkanoyl, $NR_7R_8$ or $SR_7$; wherein said alkyl, alkoxy, and alkanoyl are optionally substituted with halogen, amino, hydroxy, carboxyl, alkoxy or alkoxycarbonyl. In one embodiment $R_9$ is H, halogen alkyl, alkoxy, halo, nitro, cyano, wherein said alkyl and alkoxy are optionally substituted with hydroxy, halogen, alkoxy, aryl and aryloxy; and $R_{11}$ is H. In another embodiment $R_9$ is H, methoxy, ethoxy, ethyl, propyl ethynyl, Cl, I, propyn-1-yl or 1-chlorovinyl. In another embodiment $R_9$ is ethyl. In another embodiment $R_9$ is ethoxy.

$R_{11}$ is selected from the group consisting of H, halo, nitro, cyano, $C_1$–$C_6$ alkyl, $C_6$–$C_{10}$ aryl, $NR_7R_8$, $OR_7$, $SR_7$, $C_1$–$C_6$ alkyl-C(O)$R_7$, $C_1$–$C_6$ alkyl-C(O)$NR_7R_8$, $C_1$–$C_6$ alkyl-C(O)$OR_7$, $C_1$–$C_6$ alkyl-OC(O)$R_7$, $C_1$–$C_6$ alkyl-O$R_7$, $OC_1$–$C_6$ alkyl-C(O)$R_7$, $OC_1$–$C_6$ alkyl-C(O)$OR_7$, $OC_1$–$C_6$ alkyl-OC(O)$R_7$, O—$C_1$–$C_6$ alkyl-O$R_7$, $OC_1$–$C_6$ alkyl-C(O)$NR_7R_8$, $C_1$–$C_6$ haloalkyl, $OR_{12}$, $C_1$–$C_6$ alkyl-$R_{12}$, O—$C_1$–$C_6$ alkyl-$R_{12}$, C(O)$OR_7$, C(O)$OR_{12}$, C(O)$NR_7R_8$, OC(O)$NR_7R_8$, $NR_7$C(O)$R_7$, $NR_7$C(O)$R_{12}$, $NR_7$C(O)—$NR_7R_8$, $NR_7$C(O)$OR_7$, $NR_7$C(O)$OR_{12}$, $NR_7$S(O)$_n$—$R_1$, $NR_7$S(O)$_n$—$R_7$ and $NR_7$S(O)$_n$—$R_{12}$, where $R_7$ and $R_8$, independently, are H or unsubstituted or substituted $C_1$–$C_6$ alkyl, $R_{12}$ is unsubstituted or substituted $C_6$–$C_{10}$ aryl or heterocyclic as defined above and n is 1 or 2. In a particular embodiment $R_{11}$ is $NR_7C_1$–$C_6$ alkyl-C(O)$NR_7R_8$, $NR_7$S(O)$_n$—$R_7$ or N $R_7$S(O)$_n$—$R_{12}$ where $R_7$ and $R_{12}$ are unsubstituted or substituted as defined above. Suitable substituted $R_7$ and $R_{12}$ include these groups substituted as described above, for example, having 1 or 2 $C_1$–$C_6$ alkoxy, $C_1$–$C_6$ alkoxy- –$C_1$–$C_6$ alkoxy, halo, $C_1$–$C_6$ haloalkyl, $C_1$–$C_6$ hydroxyalkyl, $C_1$–$C_6$ aminoalkyl, OC(O)—$C_1$–$C_6$ alkyl, C(O)O—$C_1$–$C_6$ alkyl, $C_1$–$C_6$ alkyl C(O)$OR_7$, $C_1$–$C_6$ alkyl OC(O)$R_7$ or C(O)OH. In one embodiment $R_{11}$ is H.

In another embodiment, Y is S(O)$_n$—$R_1$ where n is 1 or 2. In this embodiment, $R_1$ may be as defined above and each of the remaining variables may be independently selected to have any of the definitions described above.

In another embodiment, A and B are independently CH or $CR_3$, where $R_3$ is H, $C_{1-6}$ alkyl or OH, where the remaining variables may be independently selected to have any of the definitions described above.

In another embodiment, $R_6$ is H or $R_3$ is CH, where the remaining variables may be independently selected to have any of the definitions described above.

In another embodiment, X is a carbonyl group (C═O), where the remaining variables may be independently selected to have any of the definitions described above.

Table 1 sets forth examples of some exemplary unsubstituted amine compounds of the invention having the general Formula II. A group of specific compounds is disclosed in this table and is obtained by selecting all unique combinations of substituents, one from each column of the table, for each variable and combining these groups with the structure disclosed above Table 1.

TABLE 1

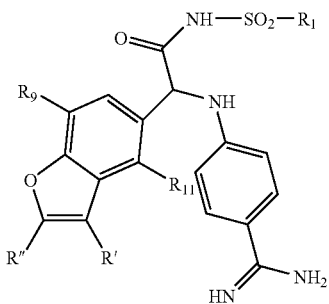

II

| R' | R" | $R_9$ | $R_{11}$ | $R_1$ |
|---|---|---|---|---|
| Cl | H | OEt | H | Me |
| methyl | Me | OMe | NMeSO$_2$Me | Et |
| ethyl | Pr | CH$_2$CH$_3$ | Ph | Pr |
| propyl | —(CH$_2$)$_2$—OH | CH═CH$_2$ | Naphthyl | Bu |
| hydroxy-ethyl | —(CH$_2$)$_2$—O-Benzoyl | CCH | H | iPr |
| benzoyloxy-ethyl | ethyl | CH$_2$CCH | NHSO$_2$Me | iBu |
| H | propyl | H | NPrSO$_2$Me | sBu |
| H | t-butyl | Pr | N(CH$_2$CO$_2$H)SO$_2$Me | Ph |
| H | hydroxymethyl | Cl | NMeSO$_2$CH$_2$—CO$_2$H | O-tolyl |
| H | 1-methoxy-1-methylethyl | SCH$_3$ | NHSO$_2$CH$_2$—CO$_2$H | CH$_2$CH$_2$—CO$_2$H |
| H | 1-hydroxy-1-methylethyl | SCH$_2$CH$_3$ | NHCOCH$_3$ | CH$_2$CH$_2$—CONH$_2$ |
| H | methoxymethyl | NHCH$_3$ | NHCOCH$_2$—CO$_2$H | CH$_2$CH$_2$—CO$_2$Me |
| H | aminomethyl | NHCH$_2$CH$_3$ | NHSO$_2$-thiophene | p-tolyl |
| H | N-dimethylaminomethyl | H | NHSO$_2$CH$_2$—CO$_2$H | 4-chlorophenyl |
| H | N-acetylaminomethyl, | H | NHSO$_2$CH$_2$—CO$_2$Me | 4-aminomethylphenyl |
| H | N-acetyl-N-methylaminomethyl | H | OCH$_2$CO$_2$H | 4-aminophenyl |
| H | acetylethyl | H | pyridyl | 2-chlorophenyl |

TABLE 1-continued

| R' | R" | $R_9$ | $R_{11}$ | $R_1$ |
|---|---|---|---|---|
| H | propanoyl | H | H | 3-nitrophenyl |
| H | acetyl | H | H | 1-naphthyl |
| H | ethyloxycarbonyl-oxymethyl | H | H | 2-thiophene |
| H | acetyloxyethyl | H | H | 3-thiophene |
| H | t-butylcarbonyl-oxyethyl | H | H | 2-furan |
| H | benzoyloxyethyl | H | H | 3-furan |
| H | propanoyloxyethyl | H | H | $CH_2CH(NH_2)CH_3$ |
| H | trichloroacetyloxyethyl | H | H | pyridyl |
| H | 3,5-diCF$_3$-benzoyloxyethyl | H | H | 2-naphthyl |

Particular compounds of the invention include:

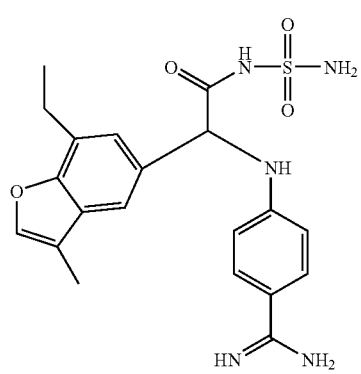

8

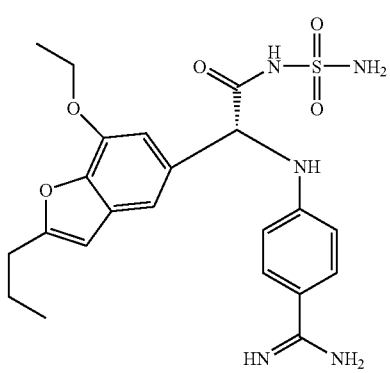

13

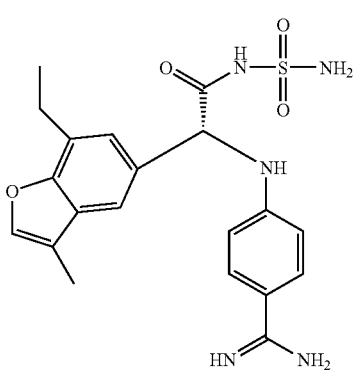

12

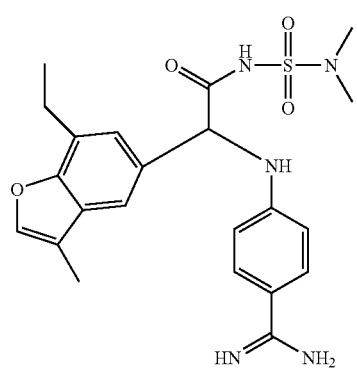

14

15
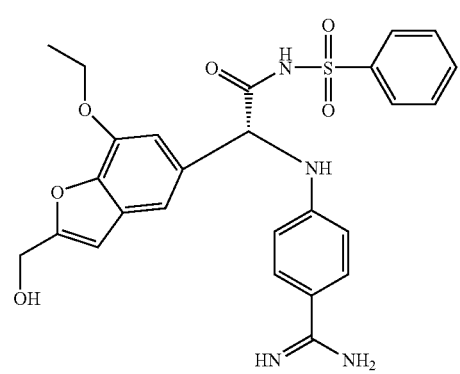
16
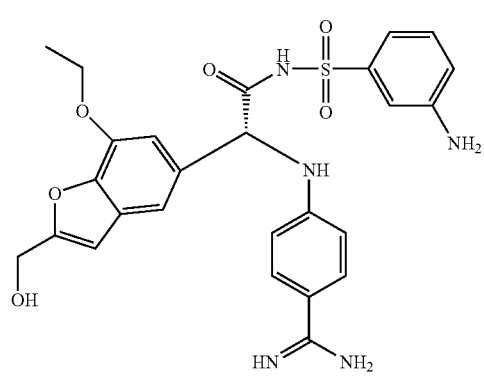
17
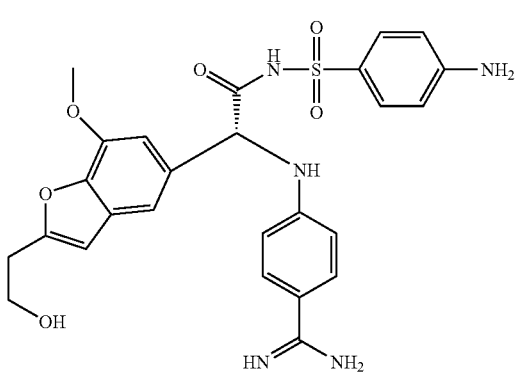
18
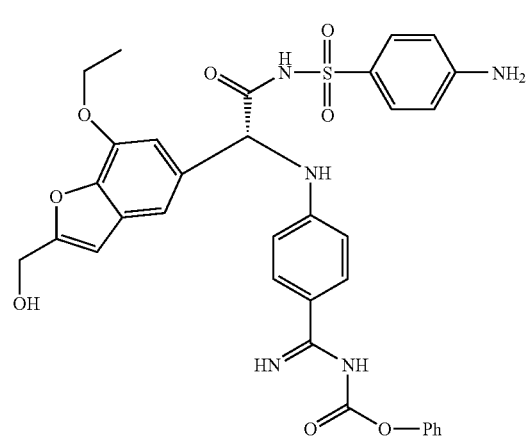
19
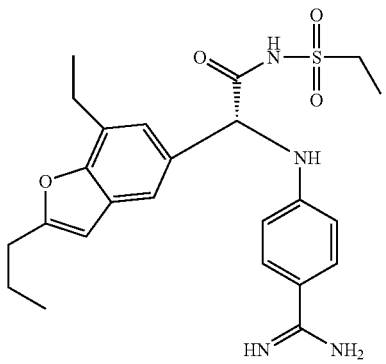
20
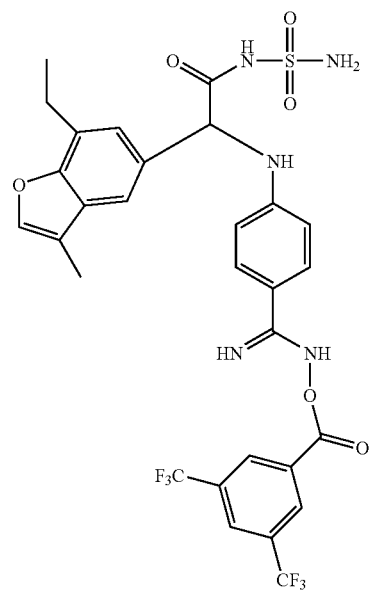
21
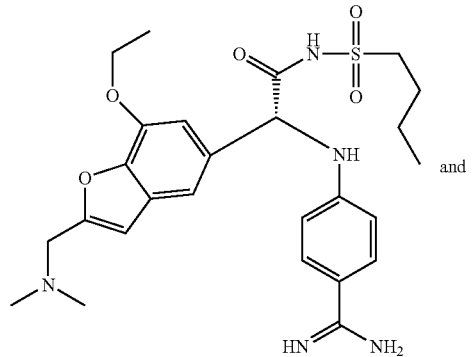 and

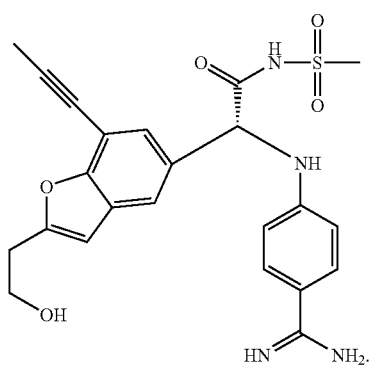
22
Other compounds of the invention include:
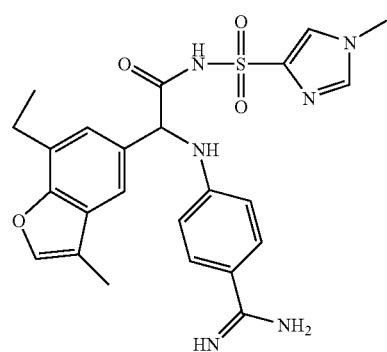
23
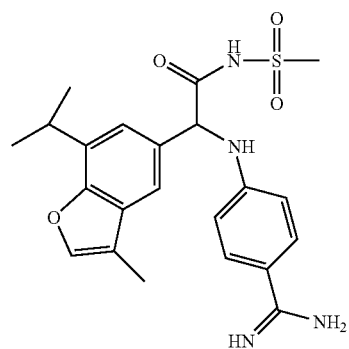
24
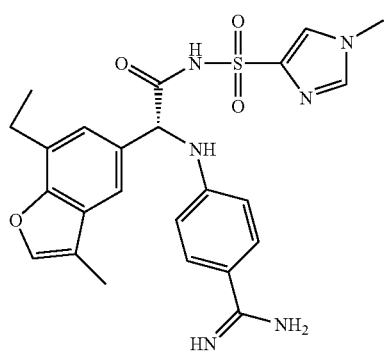
25
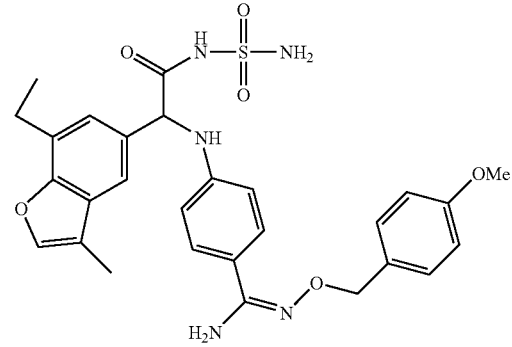
26
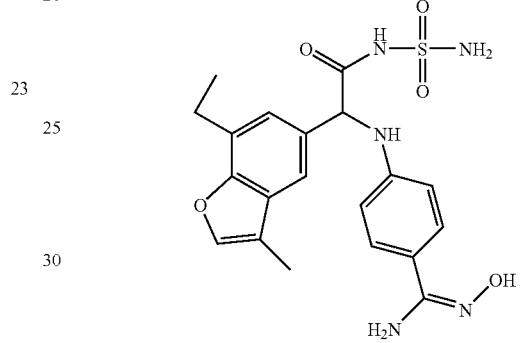
27
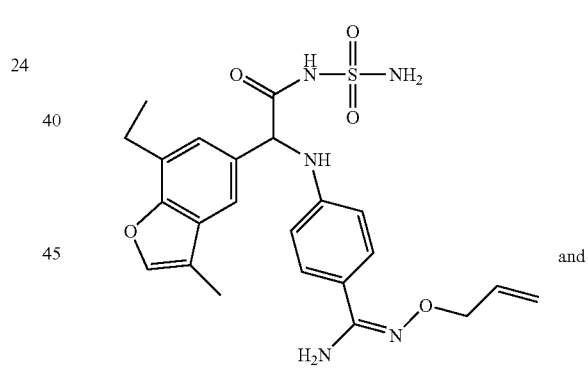
28
and
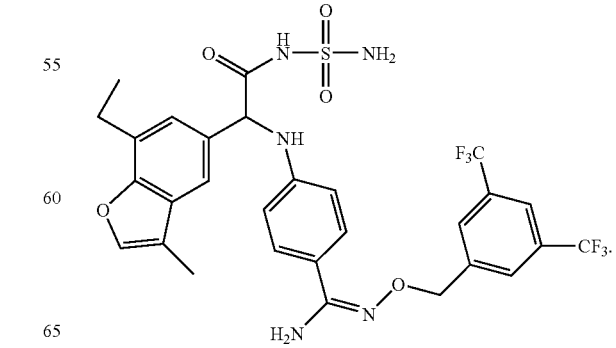
29

Formula I compounds of the invention include those having the formulas:

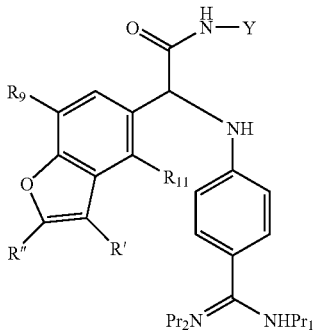

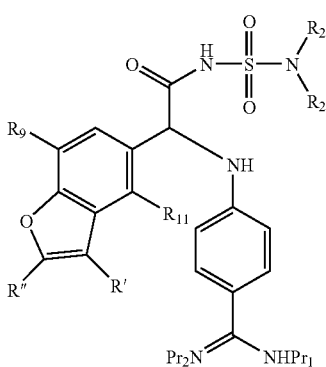

Compounds of the invention also include novel intermediates which are useful for the preparation of Formula I compounds. Such intermediates include compounds of Formula III:

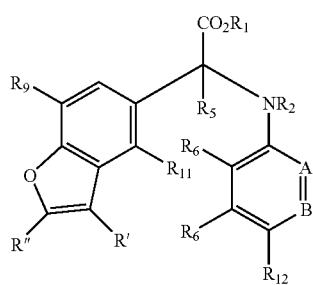

wherein
A and B are independently CH, $CR_3$ or N;
R' and R" are each independently H, carboxyl, $C_1$–$C_6$ alkyl, $C_1$–$C_6$ alkoxy, $C_1$–$C_6$ alkanoyl, $C_1$–$C_6$ alkanoyloxy or $C_1$–$C_6$ alkoxycarbonyl; wherein said alkyl, alkoxy, alkanoyl, alkanoyloxy and alkoxycarbonyl groups are optionally substituted with amino, hydroxy, alkoxy, acyl, acyloxy, a substituted or unsubstituted carbocycle or heterocycle; and one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—;

$R_1$ is $C_1$–$C_6$ alkyl, $C_2$–$C_6$ alkenyl, $C_2$–$C_6$ alkynyl, $C_3$–$C_6$ cycloalkyl, phenyl, naphthyl, benzyl or heteroaryl;

each $R_2$ is, independently, H, alkyl, substituted alkyl, aryl, substituted aryl, $C(O)R_7$ or $C(NH)R_7$, or the two $NR_2$ and $NR_2$ groups together form a heterocycle;

$R_3$ is H, $C_1$–$C_6$ alkyl, $C_1$–$C_6$ alkoxy, halogen or OH;

$R_5$ is selected from the group consisting of H, unsubstituted or substituted $C_1$–$C_6$ alkyl, unsubstituted or substituted alkoxyalkyl, unsubstituted or substituted haloalkyl, unsubstituted or substituted aryl, alkyl-$OR_7$, alkyl-$NR_7R_8$, alkyl-$OC(O)R_7$, alkyl-$C(O)OR_7$, alkyl-$C(O)R_7$, $OC(O)R_7$, $C(O)OR_7$, $C(O)R_7$ and members in which the alkyl, $R_7$ or $R_8$ is substituted with 1–3 F, Cl, Br, I, $OR_7$, $SR_7$, $NR_7R_8$, $OC(OR_7)$, $C(O)OR_7$, $C(O)R_7$, $C(O)NR_7R_8$, $NHC(NH)NH_2$, $PO_3$, unsubstituted or substituted indolyl or unsubstituted or substituted imidazolyl groups;

$R_6$ is selected from the group selected from H, $C_1$–$C_6$ alkyl, $C_1$–$C_6$ alkyl-$OR_7$, $C_1$–$C_6$ alkyl-N $R_7R_8$, $C_1$–$C_6$ haloalkyl, halo, cyano, $OR_7$, $SR_7$, $NR_7R_8$, $C(O)OR_7$, $C(O)R_7$ and $OC(O)R_7$;

$R_7$ and $R_8$ are independently H or $C_1$–$C_6$ alkyl;

$R_9$ is H, halogen, hydroxy, $C_1$–$C_6$ alkyl, alkoxy, alkanoyl, $NR_7R_8$ or $SR_7$; wherein said alkyl, alkoxy, and alkanoyl are optionally substituted with halogen, amino, hydroxy, carboxyl, alkoxy or alkoxycarbonyl;

$R_{11}$ is selected from the group consisting of H, halo, nitro, cyano, $C_1$–$C_6$ alkyl, $C_6$–$C_{10}$ aryl, $NR_7R_8$, $OR_7$, $SR_7$, $C_1$–$C_6$ alkyl-$C(O)R_7$, $C_1$–$C_6$ alkyl-$C(O)NR_7R_8$, $C_1$–$C_6$ alkyl-$C(O)OR_7$, $C_1$–$C_6$ alkyl-$OC(O)R_7$, $C_1$–$C_6$ alkyl-$OR_7$, $OC_1$–$C_6$ alkyl-$C(O)R_7$, $OC_1$–$C_6$ alkyl-$C(O)OR_7$, $OC_1$–$C_6$ alkyl-$OC(O)R_7$, $O$—$C_1$–$C_6$ alkyl-$OR_7$, $OC_1$–$C_6$ alkyl-$C(O)NR_7R_8$, $C_1$–$C_6$ haloalkyl, $OR_{12}$, $C_1$–$C_6$ alkyl-$R_{12}$, $O$—$C_1$–$C_6$ alkyl-$R_{12}$, $C(O)OR_7$, $C(O)OR_{12}$, $C(O)NR_7R_8$, $OC(O)NR_7R_8$, $NR_7C(O)R_7$, $NR_7C(O)R_{12}$, $NR_7C(O)$—$NR_7R_8$, $NR_7$—($C_1$–$C_6$ alkyl)-$C(O)$—$NR_7R_8$, $NR_7C(O)OR_7$, $NR_7C(O)OR_{12}$, $NR_7S(O)_n$—$R_1$, $NR_7S(O)_n$—$R_7$ and $NR_7S(O)_n$—$R_{12}$, wherein $R_{12}$ is unsubstituted or substituted $C_6$–$C_{10}$ aryl or heterocycle and n is 1 or 2;

$R_{12}$ is selected from H, Cl, Br, I, CN, C(=$NPr_2$)($NHPr_1$), COOH, C(O)—$NR_7R_8$ and $COOR_1$;

$Pr_1$ and $Pr_2$ are independently H, hydroxy, alkyl, alkoxy, alkanoyl, alkanoyloxy, alkoxycarbonyl, aryloxy, or arylalkoxy;

said alkyl, alkoxy, alkanoyl, alkanoyloxy, alkoxycarbonyl, aryloxy or arylalkoxy are independently and optionally substituted with hydroxy, halogen, carboxyl, alkyl, halosubstituted alkyl, alkoxy, a carbocycle or a heterocycle;

said carbocycle and heterocycle are optionally substituted with 1–5 hydroxy, alkoxy, carboxyl, alkyl, or halosubstituted alkyl; and one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—;

acid and base addition salts and prodrugs thereof.

One embodiment of Formula III compounds include compounds having the formula:

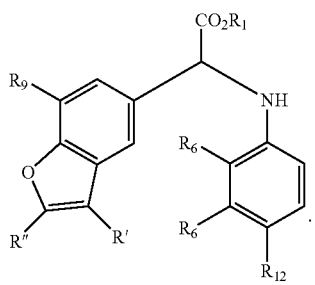

Synthesis of the Benzofuran Compounds

Compounds of the present invention can be prepared by methods employing standard chemical methodologies described and referenced in standard textbooks (e.g. Smith, M. and March, J. "March's Advanced Organic Chemistry: Reactions, Mechanisms, and Structure, 5th Edition" McGraw-Hill, New York, 2001); Collman, J. P., Hegedus, L. S., Norton, J. R., Finke, R. G. "Principles and Applications of Organotransition Metal Chemistry" University Science, Mill Valley, 1987; Larock, R. C. "Comprehensive Organic Transformations" Verlag, New York, 1989). Reagents for the transformations elucidated in the embodiments of the invention are standard and may be found in standard reference books and series such as "Fiesers' Reagents for Organic Synthesis" Volumes 1–22 (John Wiley, New York).

Benzofuran intermediates may be prepared using standard organic synthetic techniques which can be employed in the various synthetic routes described below to give the desired final benzofuran compound of the invention. An exemplary benzofuran aldehyde intermediate (c) having substituents at R'', $R_9$ and $R_{11}$ may be prepared according the following scheme

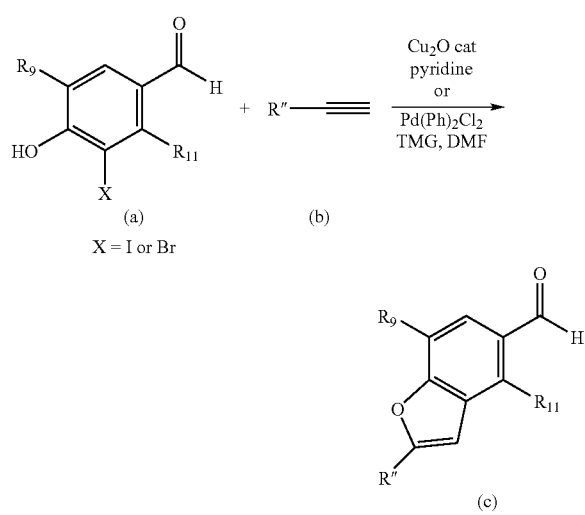

wherein starting compound (a) is reacted with R''-substituted alkyne (b) in pyridine in the presence of copper catalyst in a Castro-Stephens coupling reaction (see J Med Chem, 1996, 39(17):3269) or alternatively in DMF with palladium catalyst and strong base tetramethylguanidine. The resulting aldehyde intermediate (c) is conveniently employed in various synthetic routes described below to give the final benzofuran compound of the invention. In one embodiment $R_{11}$ is H. Alternatively, the starting compound (a) is coupled to a cyanoaniline to give intermediate (d) prior to prior to cyclization to give intermediate (e) according to the following scheme.

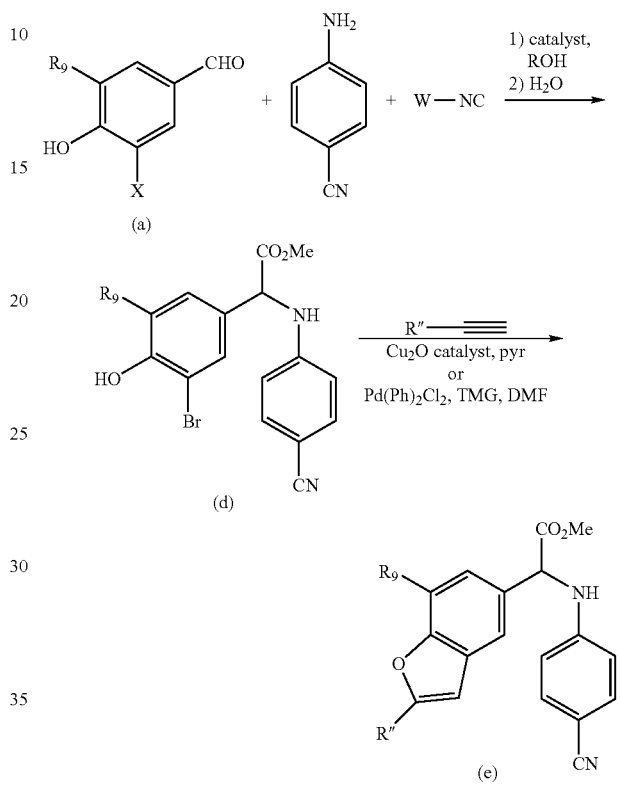

The condensation of (a) with cyanoaniline is performed in the presence of a catalyst, e.g. a Lewis acid catalyst, and an alkyl alcohol (ROH), such as a lower, i.e. $C_1$–$C_6$, alkyl alcohol like methanol, ethanol, i-propanol, etc., followed by hydrolysis of the intermediate. Hydrolysis conditions may include an excess of water, generally 10 or more equivalents of water. Suitable Lewis Acids include $BF_3$ etherate, $AlCl_3$, etc. W—NC is an isonitrile in which W may be any suitable hydrocarbon group, generally an alkyl, carbocycloalkyl, or aralkyl group, for example having no more than about 12 carbon atoms. One isonitrile is benzyl isonitrile. The ester product may be purified by standard techniques, including high pressure liquid chromatography (HPLC), column chromatography, recrystallization, etc. the cyano group may be converted into an amidino group ($C(NH)NH_2$), for example, using known procedures, such as the Pinner reaction. The cyano group of intermediate compound (e) is converted to amidine by reacting with hydroxylamine, for example in an alcohol solvent, followed by reduction with Raney Ni in an alcohol solvent, or may be reacted first with ethanolic HCl and then with alcoholic ammonia. Alternatively, a modified Pinner reaction using pyridine/diethylamine (1/1)/hydrogen sulfide followed by methyl iodide/acetonitrile and then ammonium acetate/ethanol may be used to convert the cyano group to the desired amidino compound.

Another exemplary benzofuran aldehyde intermediate (c) having substituents at R', $R_9$ and $R_{11}$ may be prepared according the following scheme

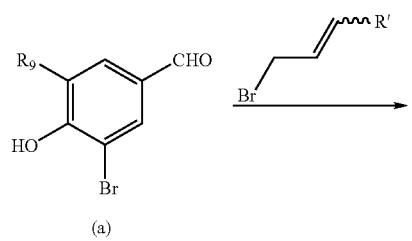
(a)

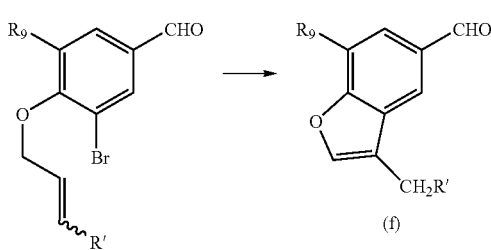
(f)

wherein starting compound (a) is reacted with an allylbromide reagent and $Cs_2CO_3$ in DMF to give allyl substituted compound with is then cyclized to give benzofuran intermediate (f) according to the procedures of Larock et al (Tetrahedron Lett, 1988, 29:4687) by reacting with $Na_2CO_3$, $HCO_2Na$, $Bu_4NCl$ in dimethylacetamide (DMA), then palladium (II) acetate. Alternatively the allyl substituted phenol can be coupled to a cyanoaniline compound prior to cyclization to give intermediate (g) according to the following scheme.

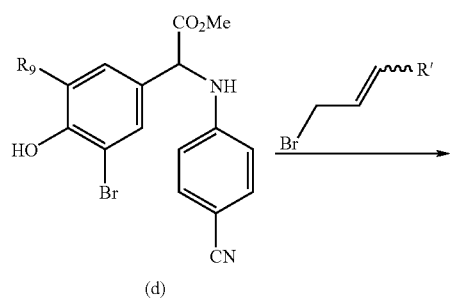
(d)

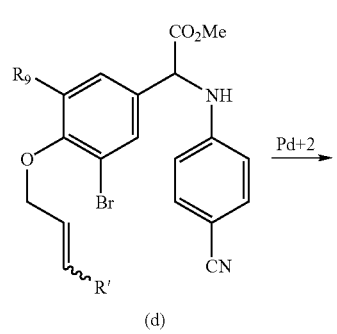
(d)

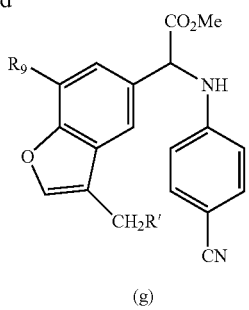
(g)

Starting compound (a) is commercially available or is prepared using standard organic synthetic techniques. In a particular embodiment, compound (a) in which $R_9$ is alkyl may be prepared according to the following scheme:

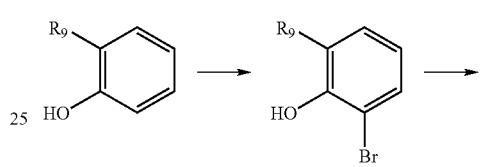

(a')

wherein the starting 2-alkylphenol is brominated by reacting with N-bromosuccinimide in diisopropylethylamine and $CH_2Cl_2$, or some other electrophilic brominating agent, and then refluxing with hexamethylene tetraamine and acetic acid to give aldehyde (a') which then may be cyclized as described previously.

Another method of preparing substituted benzofuran intermediates is detailed in the following scheme, where a para-bromo phenolic compounds is alkylated with a halomethyl ketone, followed by acidic cyclization to form the furan, and metalation of the bromo position and acylation.

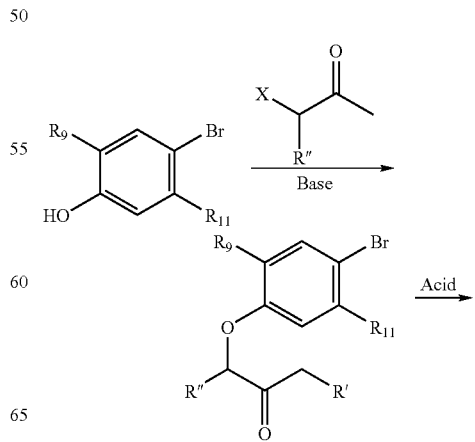

-continued

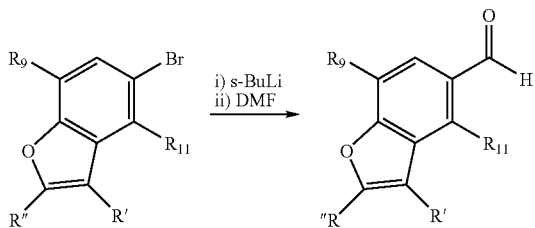

An exemplary synthesis of a benzofuran aldehyde intermediate following the above scheme is shown below:

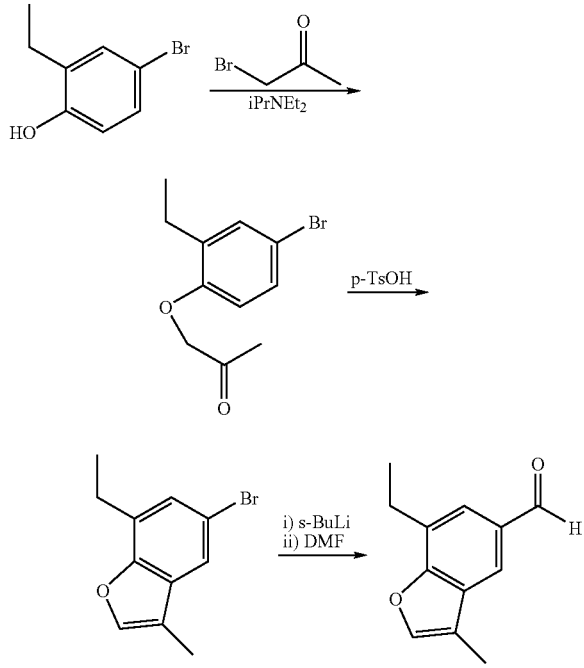

Another exemplary intermediate in the synthesis of compounds of the invention has the formula shown below:

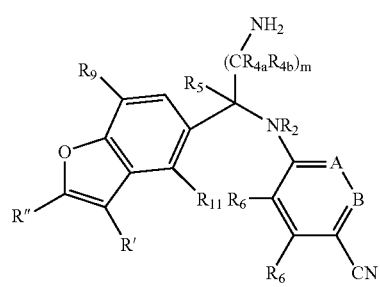

In this formula, A, B, $R_2$, $R_{4a}$, $R_{4b}$, $R_5$, $R_6$, and m have the meanings described above. This compound can be prepared using several alternative synthetic routes. After preparation, the cyano group may be converted into an amidino group (C(NH)NH$_2$), for example, using known procedures, such as the Pinner reaction. A cyano compound having the formula shown above may be reacted with hydroxylamine, for example in an alcohol solvent, followed by reduction with Raney Ni in an alcohol solvent, or may be reacted first with ethanolic HCl and then with alcoholic ammonia to yield the corresponding amidino compounds. Alternatively, a modified Pinner reaction using (1/1) pyridine/diethylamine and hydrogen sulfide, followed by methyl iodide/acetonitrile, and then ammonium acetate/ethanol will provide the desired amidino product.

One synthetic route to compounds having the formula shown above is a condensation reaction using appropriately substituted precursors as shown in the scheme below.

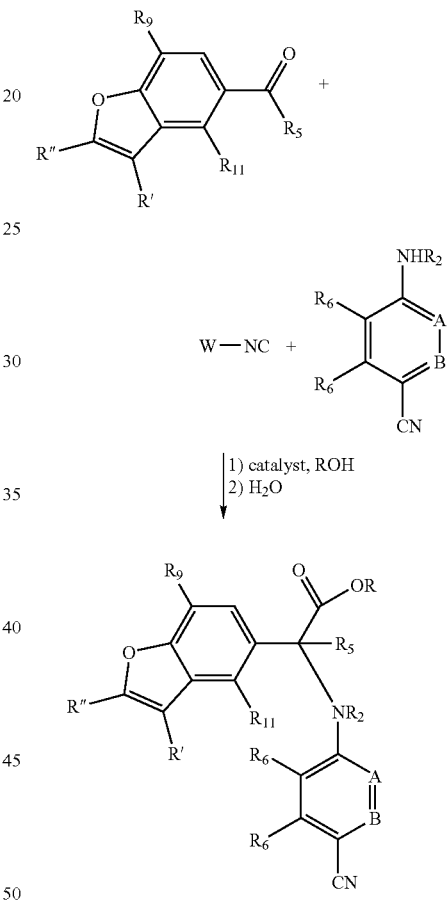

This condensation is performed in the presence of a catalyst, such as a Lewis acid catalyst, and an alkyl alcohol (ROH), such as a lower alkyl alcohol like methanol, ethanol, i-propanol, etc., followed by hydrolysis of the intermediate, with an excess of water. Suitable Lewis Acids include BF$_3$ etherate, AlCl$_3$, etc. W—NC is an isonitrile in which W may be any suitable hydrocarbon group, generally an alkyl, carbocycloalkyl, or aralkyl group, having no more than about 12 carbon atoms. An exemplary isonitrile is benzyl isonitrile. The ester product may be purified by standard techniques, including high pressure liquid chromatography (HPLC), column chromatography, recrystallization, etc.

Reduction of the resulting ester to an alcohol can be accomplished using any known reducing agent (H—) which will reduce an ester before a nitrile. Suitable reducing agents and procedures are well known in the art. See, for example, *Modern Synthetic Reactions*, H. O. House, W. A. Benjamin, Inc., Second Ed., 1972. A useful reducing agent is lithium borohydride. The alcohol may then be converted to an amine using known chemical reactions. Suitable conditions include first reacting the alcohol with hydrogen azide, DEAD, and triphenylphosphine ($PPh_3$), following by $PPh_3$ and water or first with phthalimide, DEAD and $PPh_3$, followed by hydrazine. These reactions are shown in the scheme below. Alternatively, the ester may be reacted with a reagent having a nucleophilic carbon atom to introduce suitable $R_{4a}$ groups. Such reagents may include an activated methylene carbon, for example a methylene which is adjacent to one or more strong electron withdrawing groups such as nitro ($NO_2$), carboalkoxy ($COOR_{4a}$), etc., Grignard reagents ($R_{4a}MgHal$, where Hal is a halogen), etc. and then converted to the alcohol and to the amine.

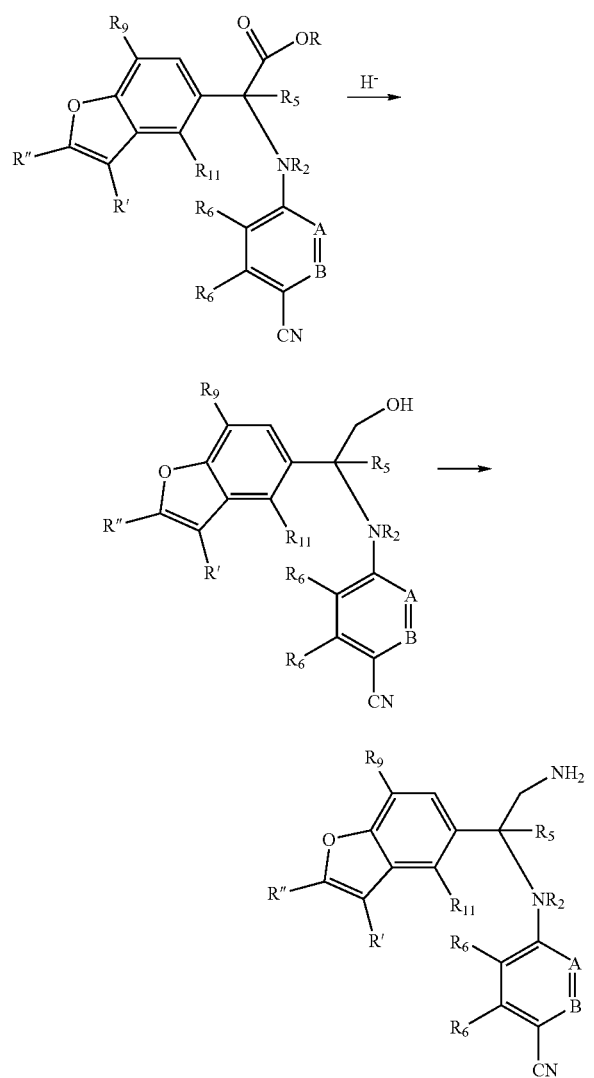

Conversion of the amine functional group to a sulfonamide and the conversion of the nitrile functional group to an amidine may be performed in any desired order. An exemplary reaction scheme is shown below.

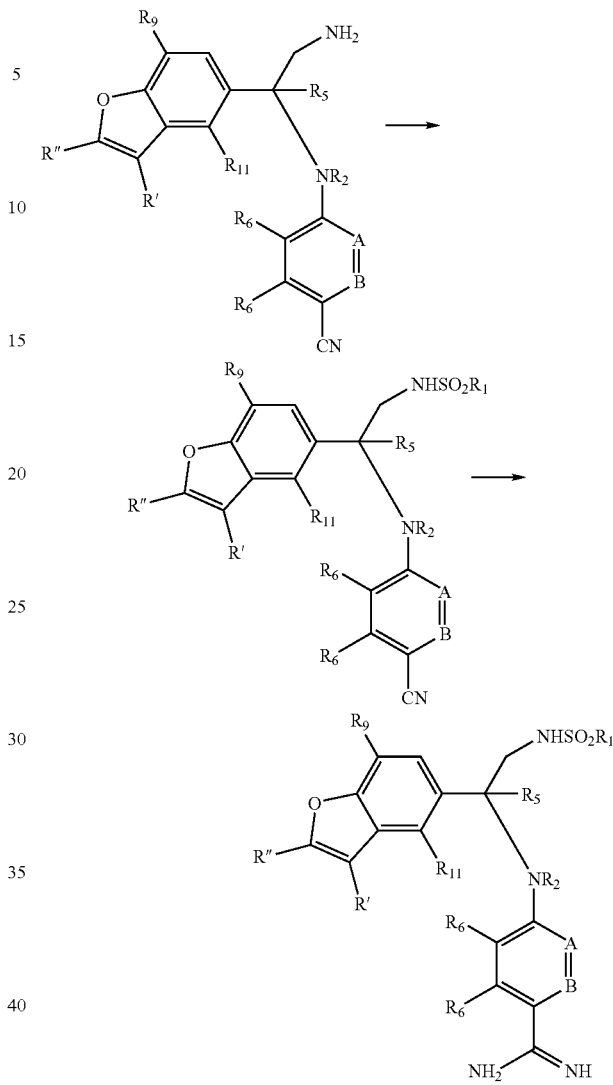

These conversions are accomplished using known chemical reactions, purification and separation procedures. The amine may be converted to a sulfonamide by reaction with an appropriately substituted sulfonyl chloride ($ClSO_2R_1$) in the presence of a base. The nitrile may be reacted with hydroxylamine in an alcohol solvent followed by reduction, for example, with Raney nickel and hydrogen, or by reaction with HCl/alcohol and then ammonia/alcohol.

An example of a suitable reaction sequence is shown below. Steps f and g are optional for conversion of $R_{11}=NO_2$ to $R_{11}=NHSO_2R_7$.

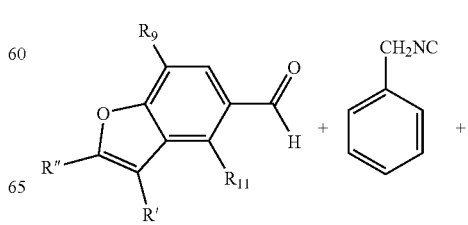

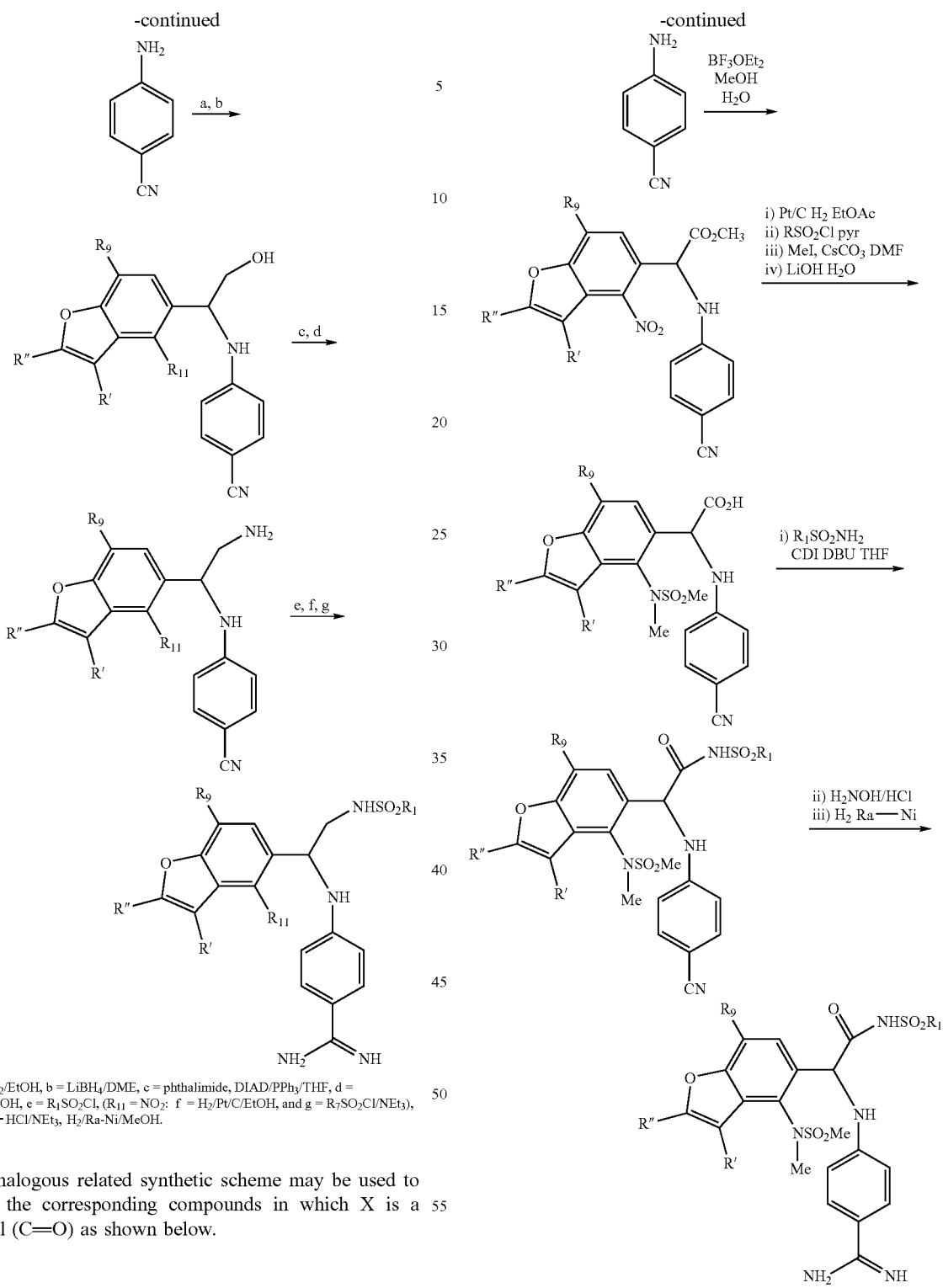

a = BF₃OEt₂/EtOH, b = LiBH₄/DME, c = phthalimide, DIAD/PPh₃/THF, d = H₂NNH₂/EtOH, e = R₁SO₂Cl, (R₁₁ = NO₂): f = H₂/Pt/C/EtOH, and g = R₇SO₂Cl/NEt₃), NH₂OH—HCl/NEt₃, H₂/Ra-Ni/MeOH.

An analogous related synthetic scheme may be used to prepare the corresponding compounds in which X is a carbonyl (C=O) as shown below.

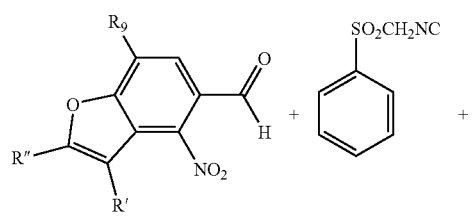

Compounds in which m=2 can be prepared using according to the scheme shown below which provides an alcohol which is homologous to the alcohol shown in the scheme above and which can be converted to an amine (and further elaborated compounds) in an analogous manner. In the scheme below, (a) is a base and (b) is a reducing agent such as LiBH₄

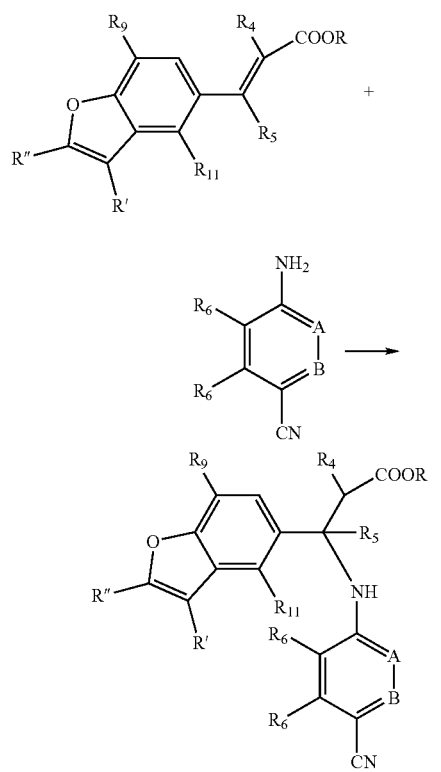
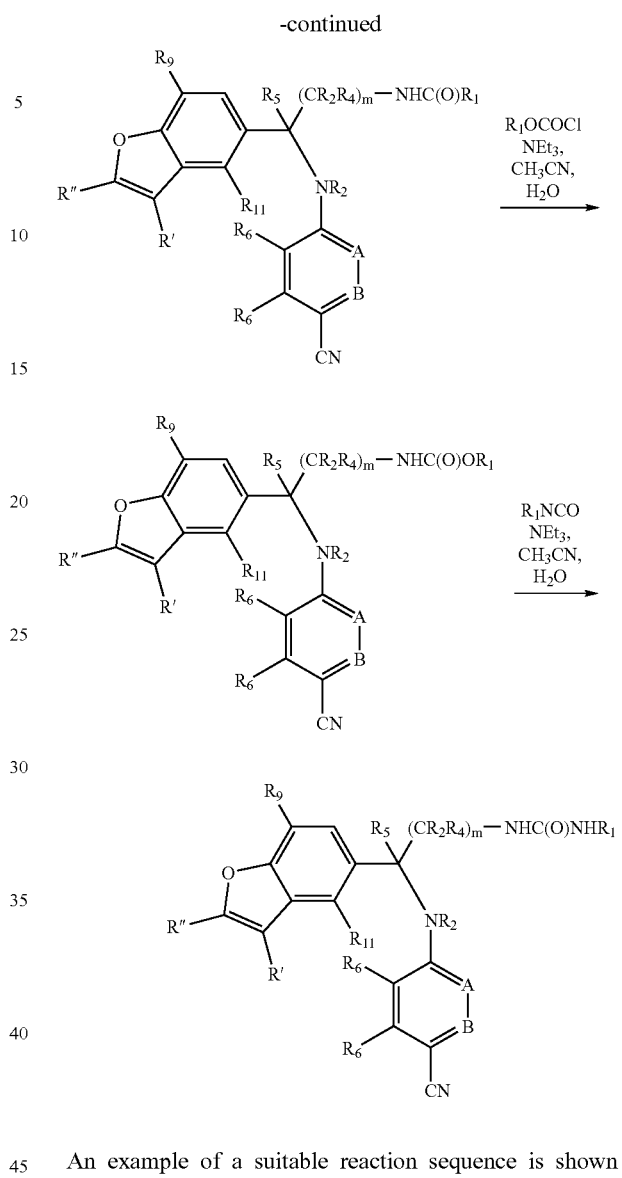
Compounds in which Y is C(O)—R$_1$; C(O)—OR$_1$; C(O)—NR$_1$R$_2$ are prepared as described above using the corresponding acyl halide (e.g. acyl chloride), alkyl haloformate (e.g. chloroformate) or isocyanate as shown in the scheme below:
An example of a suitable reaction sequence is shown below.
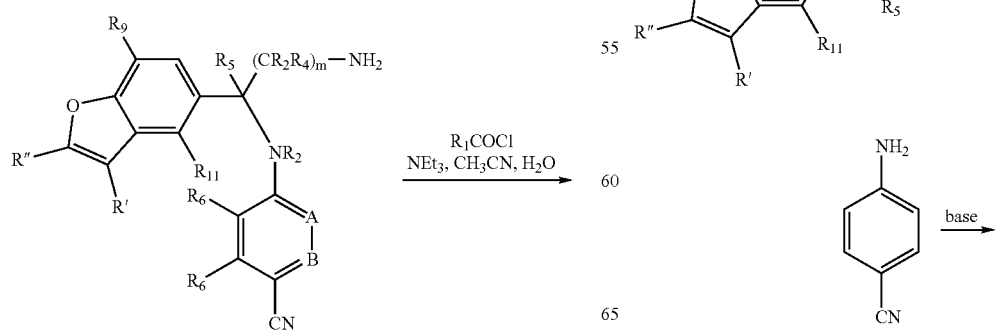

-continued

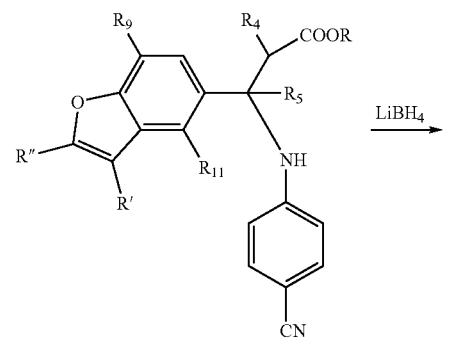

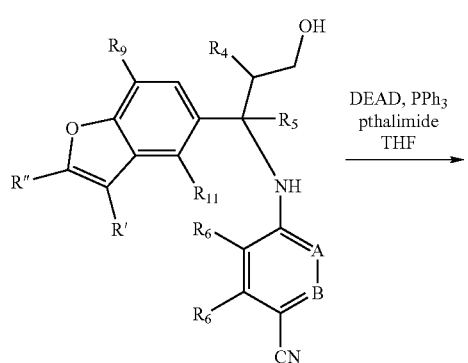

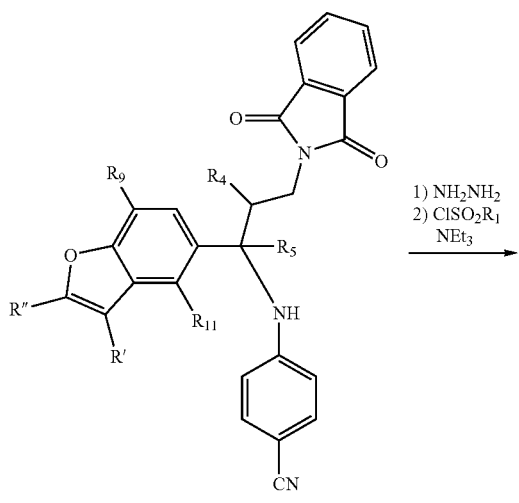

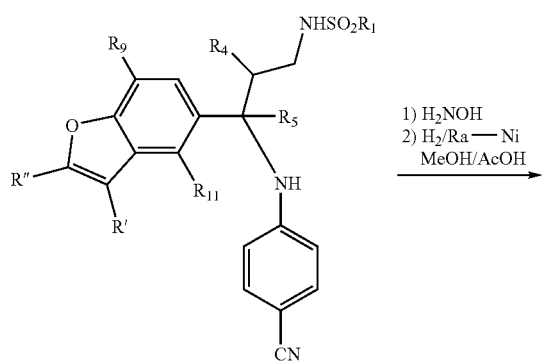

-continued

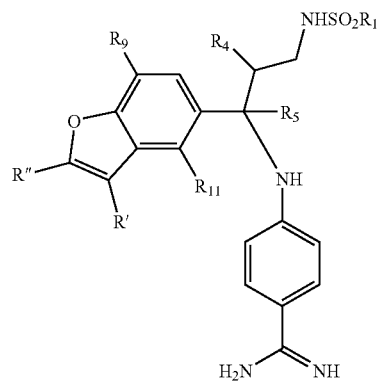

The esters resulting from the condensation reactions shown above can also function as intermediates in the synthesis of compounds in which X is a carbonyl group. Conversion of the ester to a carboxylic acid is easily performed by saponification with an alkali-metal hydroxide such as lithium, sodium, or potassium hydroxide. Coupling of a sulfonamide to the acid is accomplished by first activating the carboxylate for coupling using, for example, carbonyl diimidazole or other routine activating agents used in peptide synthesis. The second part of the coupling is done by mixing an alkyl or aryl sulfonamide with a strong base such as DBU or sodium hydride, for example in an anhydrous solvent, such as a hydrocarbon or ether solvent, e.g. tetrahydrofuran. The nitrile is converted to an amidine by methods already described.

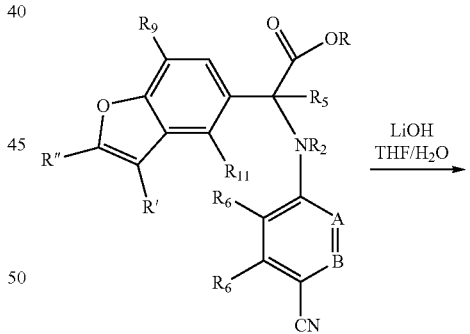

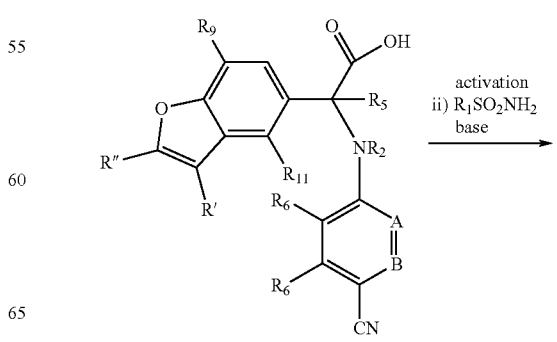

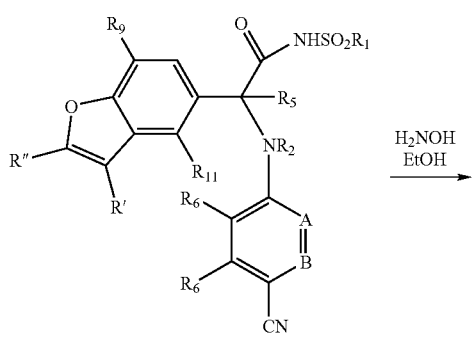

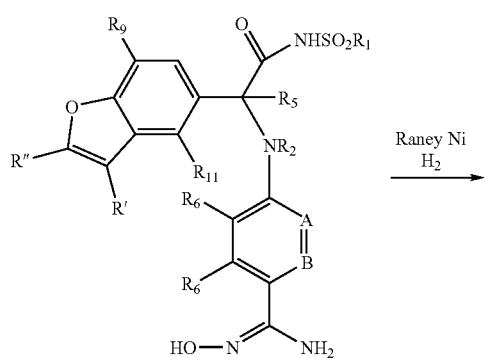

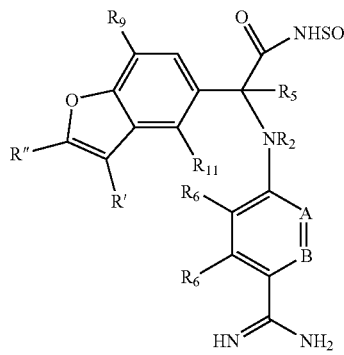

Compounds in which X is C(O) and Y is S(O)$_2$—NR$_2$R$_2$ (an acylsulfamide) may be prepared from the corresponding carboxylic acid according to the following scheme

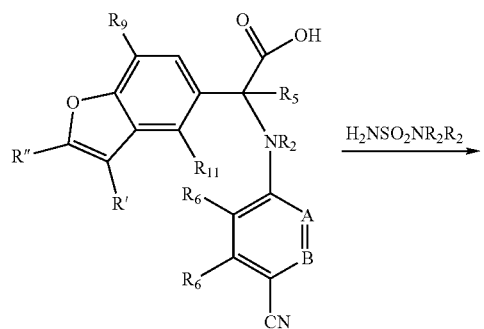

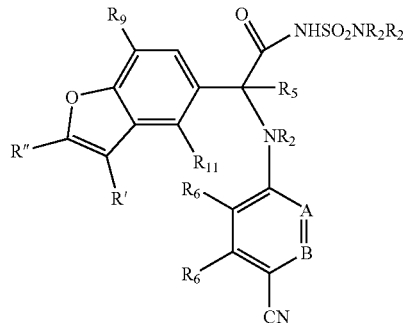

in which the carboxylic acid compound is reacted with a sulfamide H$_2$N—SO$_2$—NR$_2$R$_2$ (e.g. H$_2$N—SO$_2$—NH$_2$) and 1,1'-carbonyldiimidazole in DMF to give the sulfamide.

A further method of preparing intermediate compounds useful in preparing the compounds of the invention is shown below and involves the synthesis of imine compounds from readily available aldehydes and ketones followed by nucleophilic addition of a nucleophilic carbon atom containing reagent, i.e. in general "Nu$^-$". "Nu" may be a moiety such as CHR$_{4a}$NO$_2$, CHR$_{4a}$COOR, CH(NO$_2$)(COOR), etc., which are generated using well known Grignard reactions, reactions in which a base is used to remove a proton from the carbon atom adjacent to an electron withdrawing group (CO, COO, NO$_2$), etc.

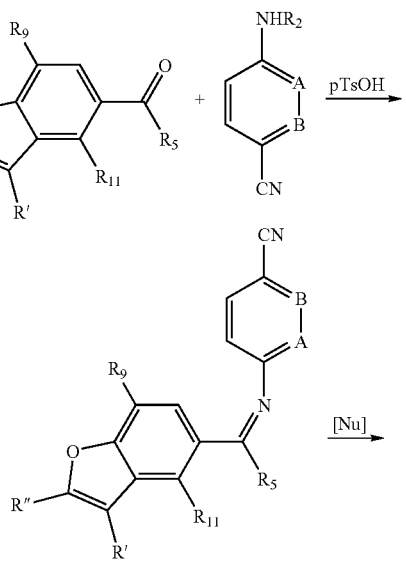

"Nu" can be converted into a group such as $CHR_{4a}NH_2$ or $CHR_{4a}CH_2OH$ or $CHR_{4a}NH_2CH_2OH$ by known reduction reactions as shown below. In these intermediates, an amino group can be further sulfonated or otherwise acylated as described above. An example of a suitable reaction sequence is shown below.

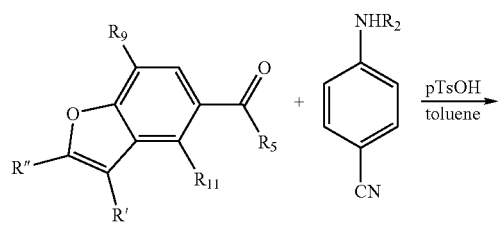

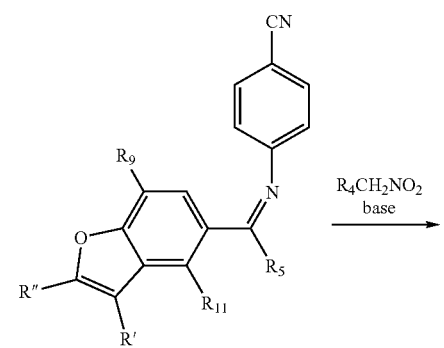

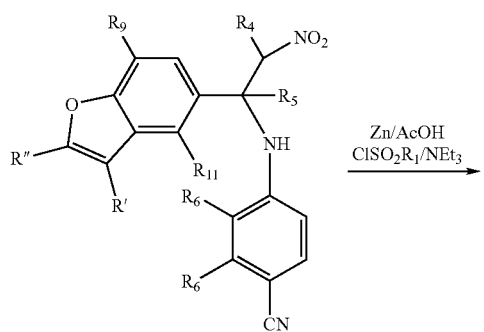

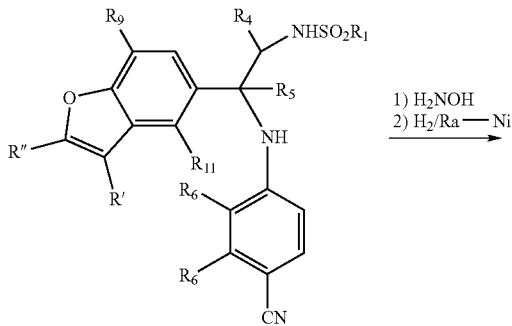

-continued

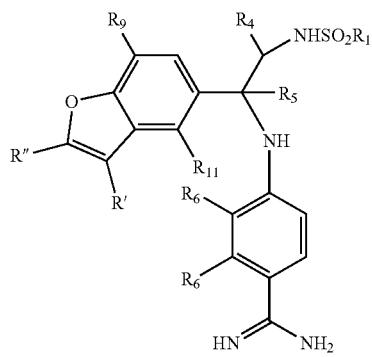

An alternative synthetic procedure can be used to prepare the alcohol intermediates described above. As shown in the scheme below, reaction of an initial styrene derivative with a peracid usually produces a mixture of products containing non-hydrogen $R_{4a}$ and/or $R_5$ substituents as shown below which can be converted without separation to the alcohol by reaction with a cyano-aniline or corresponding cyano-pyridine.

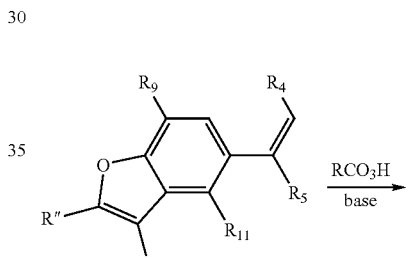

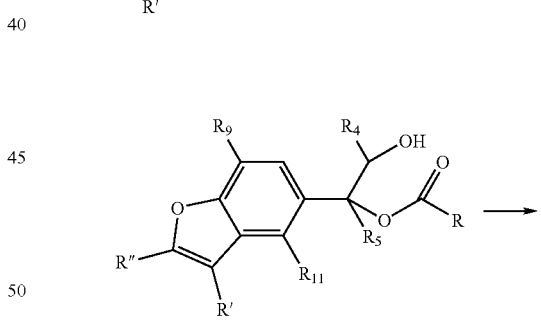

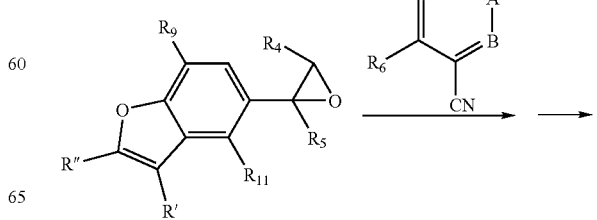

-continued

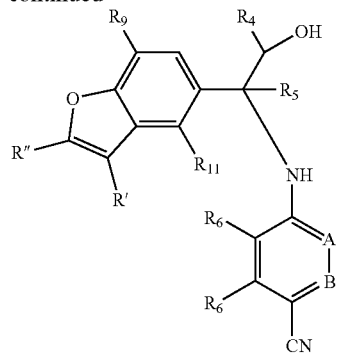

The alcohol can then be used to prepare compounds of the invention as described above.

When the corresponding compounds in which A and B are nitrogen are desired, the aniline or substituted aniline used in the reactions described above is replaced with the corresponding amino-pyridine or substituted amino-pyridine compounds.

Also included in the scope of this invention are prodrugs of the compounds described above. Suitable prodrugs include known amino-protecting and carboxyl-protecting groups which are released, for example hydrolyzed, to yield the parent compound under physiologic conditions. One class of prodrugs are compounds in which a nitrogen atom in an amino, amidino, aminoalkyleneamino, iminoalkyleneamino or guanidino group is substituted with a hydroxy (OH) group, an alkylcarbonyl (—CO—W) group, an alkoxycarbonyl (—CO—OW), an acyloxyalkyl-alkoxycarbonyl (—CO—O—W—O—CO—W) group where W is a monovalent or divalent group and as defined above or a group having the formula —C(O)—O—CP1P2-haloalkyl, where P1 and P2 are the same or different and are H, $C_1$–$C_6$ alkyl, $C_1$–$C_6$ alkoxy, cyano, $C_1$–$C_6$ haloalkyl or aryl. The nitrogen atom may be one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in WO 98/46576, published 22 Oct. 1998.

The compounds of the invention contain one or more asymmetric carbon atoms. Accordingly, the compounds may exist as diastereomers, enantiomers or mixtures thereof. The syntheses described above may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

Activity

It has been discovered that the compounds of the invention when made and selected as disclosed herein show surprising properties and unexpected results as inhibitors of serine protease enzymes, for example, factor VIIa, TF/factor VIIa, factor Xa, kallikrein and/or thrombin. These compounds are capable of inhibiting the catalytic activity of these enzymes and as such function to inhibit the coagulation cascade and prevent or limit coagulation and/or the formation of thrombi or emboli in blood vessels and/or increase the time of coagulation of blood. The compounds of the present invention, therefore, inhibit the ability of TF/factor VIIa to convert factor X to factor Xa, inhibit the ability of factor Xa to convert prothrombin to thrombin (factor IIa); and/or the ability of thrombin to convert fibrinogen to fibrin monomers.

The selectivity of the compounds of the invention as inhibitors of these enzymes can be determined using Ki values as described in the examples below.

The anti-coagulant activity of the compounds of the invention can be tested using assays. Prothrombin time (PT) and activated partial thromboplastin time (APTT) clotting time assays can be performed in pooled normal plasmas (human or various animal species) following addition of increasing concentrations of inhibitors to the plasma. Clotting times are determined using an ACL 300 Automated Coagulation Analyzer (Coulter Corp., Miami, Fla.) and commercially available reagents as follows.

PT assay: Aqueous solutions of inhibitor at various concentrations are added to pooled normal plasma in a ratio of 1 part inhibitor to 9 parts plasma. These mixtures are then added to the analyzer's sample cups. Innovin® (Dade International Inc., Miami, Fla.), a mixture of human relipidated tissue factor and $Ca^{++}$ ions is added to the reagent cup. Precise volumes of sample and Innovin® are automatically transferred to cells of an acrylic rotor that is pre-equilibrated to 37 C. Following a 2 minute incubation period, coagulation is initiated when the two components are mixed together by centrifugation. Coagulation is monitored optically and clotting time is reported in seconds. In agreement with Janson et al. (Janson, T. L., et al (1984) Haemostasis 14: 440–444) relipidated human tissue factor is a potent initiator of coagulation in all species tested. In this system, the clotting time of control plasmas (plasma plus inhibitor diluent) is typically 8 to 10 seconds. A curve is fit to the clotting time versus inhibitor concentration data and the concentration at which the PT is doubled compared to control plasma is determined for each inhibitor.

APTT assay: Inhibitor and plasma are mixed together and transferred to the ACL 300 sample cups as described above. Actin FS® and $CaCl_2$ (Dade International Inc., Miami, Fla.), are added to reagent cups 1 and 2 respectively. Precise volumes of sample and activator (Actin FS®) are automatically transferred to cells of a pre-equilibrated rotor (37 C) and mixed by centrifugation. Following a 2 minute activation period, coagulation is initiated by the addition of $CaCl_2$. Coagulation is monitored and data calculated as described in the PT method. APTT of plasma controls is typically 12 to 32 seconds, depending on the species of plasma used in the assay.

Table 2 shows assay results for TF/VIIa inhibitor 8.

TABLE 2

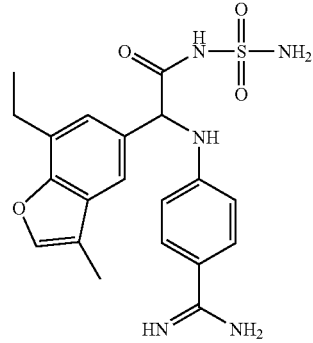

| | Ki (μM) | Selectivity |
|---|---|---|
| TFVIIa | 0.004 | 1 X |
| F. Xa | >7 | >1750 X |
| Thrombin | 0.830 | 207 X |
| Trypsin | 2.1 | 525 X |
| Plasmin | 0.880 | 220 X |
| APC | 1.44 | 360 X |
| Plasma Kallikrein | 0.082 | 20 X |
| Acetylcholinesterase | >6.8 | 1700 X |
| Complement CS1 | >6.5 | >1625 X |
| XIA | >8.0 | >2000 X |
| XIIA | >8.7 | >2175 X |
| tPA | >7.8 | >1950 X |
| Urokinase | >6.8 | >1700 X |
| Chymotrypsin | >6.9 | >1725 X |
| HGFA | 6.4 | 1600 X |

Plasma Concentrations in Rhesus Monkeys

FIG. 1 shows a graph of plasma concentrations of a benzofuran, p-aminophenyl sulfonamide VIIa inhibitor and a 3,5 bis-ethoxyphenyl, p-aminophenyl sulfonamide VIIa inhibitor following IV bolus administration in rhesus monkey following the protocol in Example 22.

Figure 2:
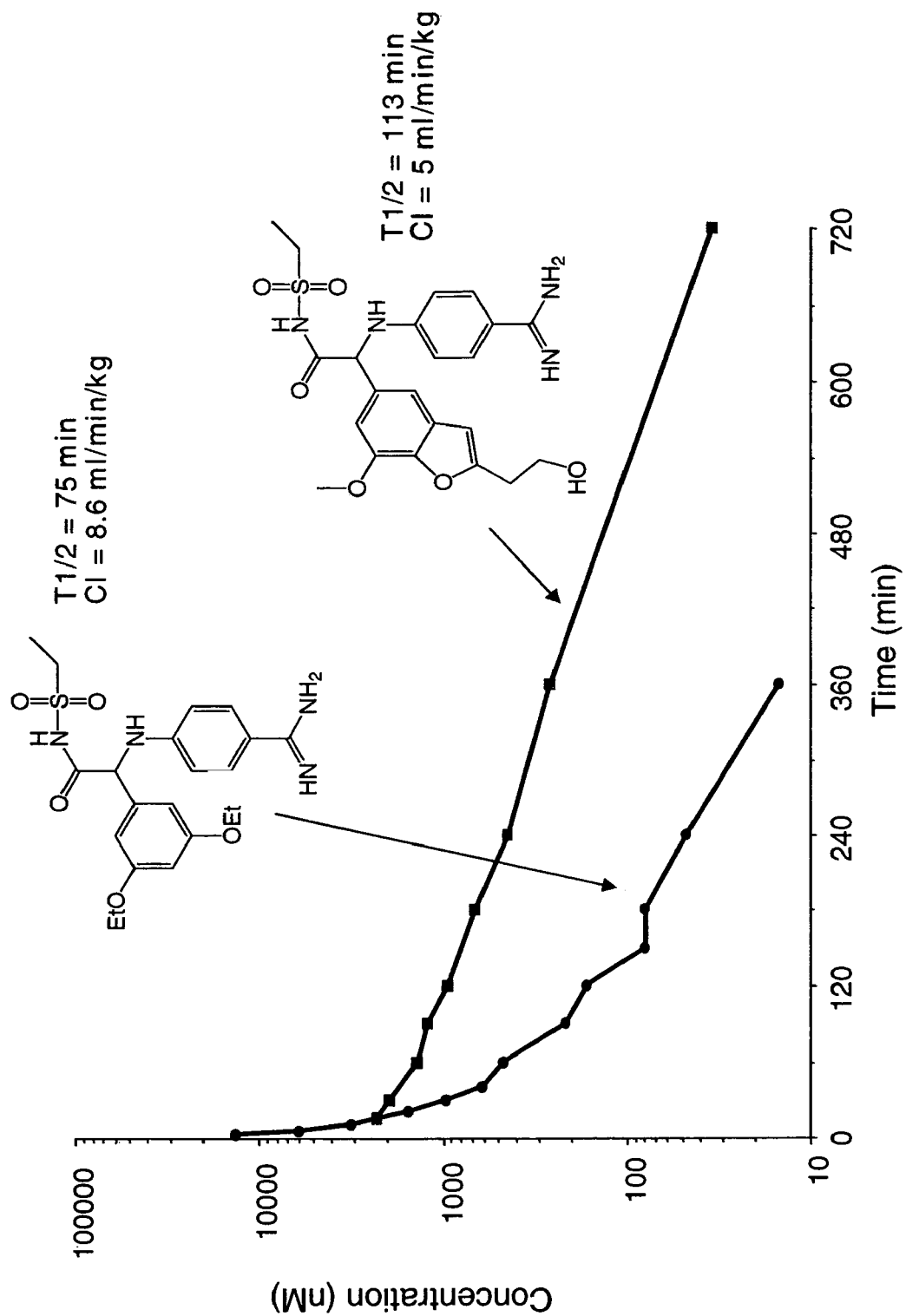
FIG. 2 shows a graph of plasma concentrations of a benzofuran, ethylsulfonamide VIIa inhibitor and a 3,5 bis-ethoxyphenyl, ethylsulfonamide VIIa inhibitor following IV bolus administration in rhesus monkey.

FIG. 2 shows a graph of plasma concentrations of a benzofuran, ethylsulfonamide VIIa inhibitor and a 3,5 bis-ethoxyphenyl, ethylsulfonamide VIIa inhibitor following IV bolus administration in rhesus monkey. The 3,5 bis-ethoxyphenyl, ethylsulfonamide has a half life of 75 minutes and clearance of 8.6 mL/min/kg body weight. The benzofuran, ethylsulfonamide VIIa inhibitor has a half life of 113 minutes and clearance of 5 mL/min/kg body weight following the protocol in Example 22.

Figure 3:
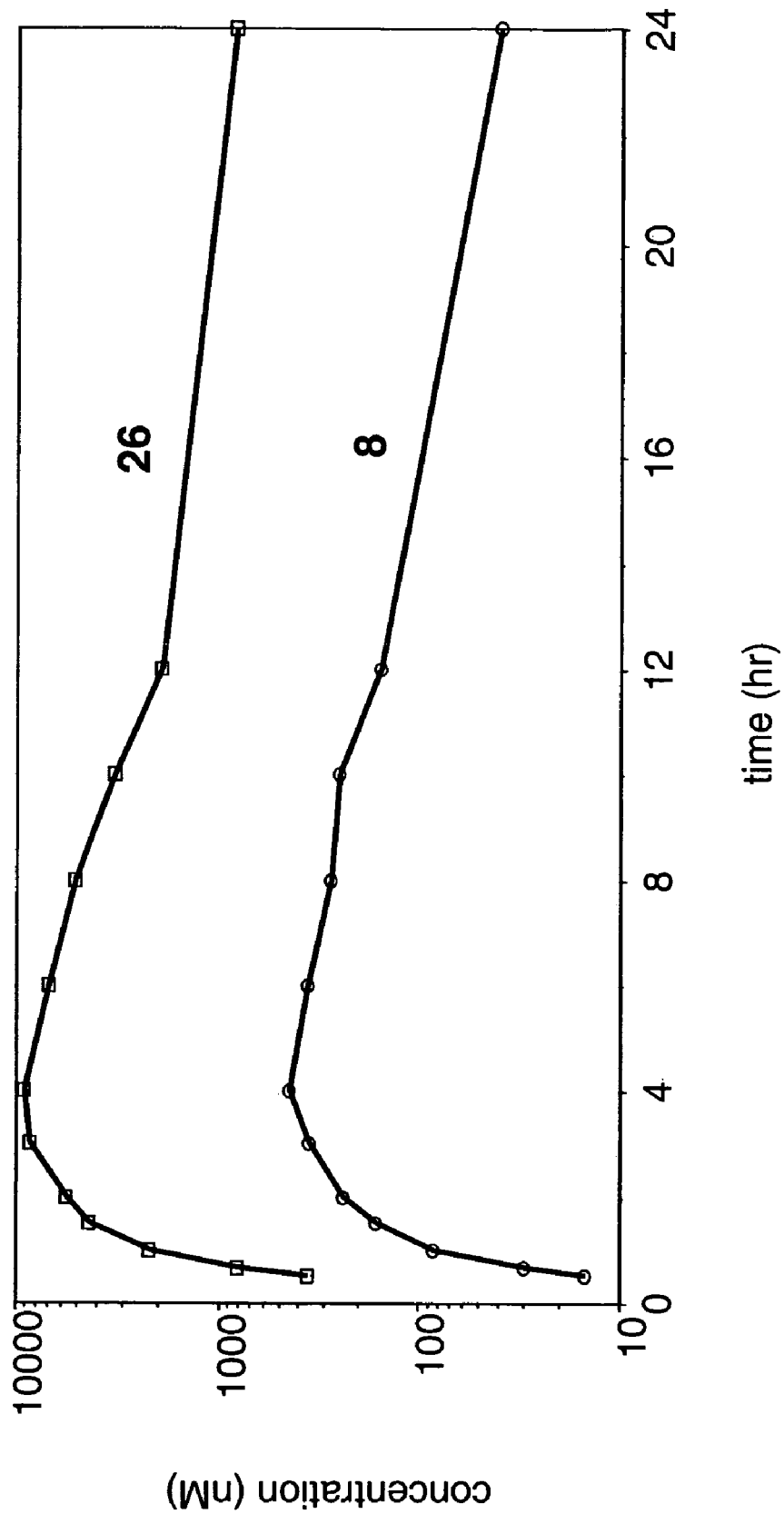
FIG. 3 shows a graph of plasma concentration in rhesus monkey of compounds 8 and 26, administered orally at 2 mg/kg.

FIG. 3 shows a graph of plasma concentration in rhesus monkey of compounds 8 and 26, administered orally at 2 mg/kg following the protocol in Example 22.

Diagnostic Reagents

The compounds of the invention are useful as diagnostic reagents in vitro for inhibiting clotting in blood drawing tubes. The use of stoppered test tubes having a vacuum therein as a means to draw blood is well known. Kasten, B. L., "Specimen Collection", Laboratory Test Handbook, 2nd Ed., Lexi-Comp Inc., Cleveland, PP 16–17, Eds. Jacobs, D. S. et al, 1990. Such vacuum tubes may be free of clot-inhibiting additives, in which case, they are useful for the isolation of mammalian serum from the blood. They may also contain clot-inhibiting additives, such as heparin salts, citrate salts or oxalate salts, in which case they are useful for the isolation of mammalian plasma from the blood. The compounds of the invention may be incorporated into blood collection tubes and function to inhibit TF/factor VIIa, factor Xa, thrombin and/or kallikrein and to prevent clotting of the mammalian blood drawn into the tubes.

When used in blood collection tubes, the compounds of the invention may be used alone, as mixtures or in combination with other clotting inhibiting compounds known in this art. The amount of the compound of the invention should be an amount sufficient to prevent or inhibit the formation of a clot when blood is drawn into the tube. These compounds may be introduced into the tubes in the same manner as known clot-inhibiting compounds such as heparin salts. Liquids are usually lyophilized using known methods. Typically, the tubes will contain about 2 to about 10 ml of mammalian blood and the compounds are added in an amount sufficient to prevent coagulation of this amount of blood. A suitable concentration is about 10–1000 nM.

Therapeutic Applications

The benzofuran compounds of the invention inhibit the formation of emboli and thrombi in the circulatory system in mammals and therefore are useful in vivo. Thromboembolic disorders have been shown to be directly related to the susceptibility of the mammal to formation of emboli and thrombi. For example, the formation of a thrombus in a veinous vessel results in thrombophlebitis, which is typically treated with rest and the administration of anticoagulants. Other conditions which can be treated with the anticoagulant compounds of the invention include, thrombolymphangitis, thrombosinusitis, thromboendocarditis, thromboangiitis, and thromboarteritis.

Mammals exposed to medical procedures such as angioplasty and thrombolytic therapy are particularly susceptible to thrombus formation. The compounds of the present invention can be used to inhibit thrombus formation following angioplasty. They may also be used in combination with antithrombolytic agents such as tissue plasminogen activator and its derivatives (U.S. Pat. Nos. 4,752,603; 4,766,075; 4,777,043; EP 199 574; EP 238 304; EP 228 862; EP 297 860; PCT WO89/04368; PCT WO89/00197), streptokinase and its derivatives, or urokinase and its derivatives to prevent arterial reocclusion following thrombolytic therapy. When used in combination with the above thrombolytic agents, the compounds of the present invention may be administered prior to, simultaneously with, or subsequent to the antithrombolytic agent.

Mammals exposed to renal dialysis, blood oxygenation, cardiac catheterization and similar medical procedures as well as mammals fitted with certain prosthetic devices are also susceptible to thromboembolic disorders. Physiologic conditions, with or without known cause may also lead to thromboembolic disorders.

Thus, the compounds described herein may be useful in treating thromboembolic disorders in mammals. The compounds described herein may also be used as adjuncts to anticoagulant therapy, for example in combination with aspirin, heparin or Warfarin (COUMADIN®) and other anticoagulant agents. The various coagulation disorders described above are treated with the compounds of the invention in such a fashion as to prevent bleeding as a result of the disorder. The application of the compounds described herein for these and related disorders will be apparent to those skilled in the art.

Compounds of this invention are also useful as intermediates generally, or as precursors of coagulation serine protease inhibitors and thus in addition to treating cardiovascular disease, these compounds may be usefully employed in metastatic disease, or for any disease where inhibition of coagulation is indicated.

Administration of Benzofuran Compounds

The benzofuran compounds of the invention may be administered by any route appropriate to the condition to be treated. Suitable routes include oral, parenteral (including subcutaneous, intramuscular, intravenous, intradermal, intrathecal and epidural), rectal, nasal, topical (including buccal and sublingual), vaginal and the like. It will be appreciated that the preferred route may vary with for example the condition of the recipient. Where the benzofuran compound is administered orally, it may be formulated as a pill, capsule, tablet, etc. with a pharmaceutically acceptable carrier or excipient. Where the benzofuran compound is administered parenterally, it may be formulated with a pharmaceutically acceptable parenteral vehicle and in a unit dosage injectable form.

Pharmaceutical Formulations of Benzofuran Compounds

Pharmaceutical, formulations of therapeutic benzofuran compounds of the invention may be prepared for various routes and types of administration. A benzofuran compound having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The pharmaceutical compositions of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01–100 mg/kg, namely about 0.1 to 20 mg/kg of patient body weight per day, with the typical initial range of compound used being 0.3 to 15 mg/kg/day.

The benzofuran compound of the invention is administered by any suitable means, including oral, topical, transdermal, parenteral, subcutaneous, intraperitoneal, intrapulmonary, and intranasal, and, if desired for local immunosuppressive treatment, intralesional administration (including perfusing or otherwise contacting the graft with the inhibitor before transplantation). Parenteral infusions include intramuscular, intravenous, intraarterial, intraperitoneal, or subcutaneous administration. Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the benzofuran compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical composition of a benzofuran compound may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

Although oral administration of protein therapeutics are disfavored due to hydrolysis or denaturation in the gut, formulations of benzofuran compound suitable for oral administration may be prepared as discrete units such as capsules, cachets or tablets each containing a predetermined amount of the benzofuran compound.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a benzofuran compound intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

A benzofuran compound of the invention may be combined in a pharmaceutical combination formulation, or dosing regimen as combination therapy, with a second compound having anticoagulant properties or is useful for treating thromboembolic disorders. The second compound of the pharmaceutical combination formulation or dosing regimen preferably has complementary activities to the benzofuran compound of the combination such that they do not adversely affect each other. Such molecules are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Benzofuran Compounds

Also falling within the scope of this invention are the in vivo metabolic products of the benzofuran compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $C^{14}$ or $H^3$) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the benzofuran compounds of the invention.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds a benzofuran compound or formulation thereof which is effective for treating the condition and may have a sterile access port (for example the container may be an intravenous solution bag or a vial having a stopper pierceable by a hypodermic injection needle). At least one active agent in the composition is a benzofuran compound of the invention. The label or package insert indicates that the composition is used for treating the condition of choice, such as cancer. In one embodiment, the label or package inserts indicates that the composition comprising the benzofuran compoun can be used to treat a thromoembolic disorder. In addition, the label or package insert may indicate that the patient to be treated is one having a thromoembolic disorder characterized by excessive bleeding. The label or package insert may also indicate that the composition can be used to treat other disorders.

The article of manufacture may comprise (a) a first container with a benzofuran compound contained therein; and (b) a second container with a second pharmaceutical formulation contained therein, wherein the second pharmaceutical formulation comprises a second compound with anticoagulant activity. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Methods of Separation

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g. an enantiomer, substantially free of its stereoisomer may be obtained by resolution of the racemic mixture using a method such as formation of diastereomers using optically active resolving agents (Eliel, E. and Wilen, S. (1994) "Stereochemistry of Organic Compounds," John Wiley & Sons, Inc.; Lochmuller, C. H., (1975) *J. Chromatogr.*, 113(3):283–302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

Under method (1), diastereomeric salts can be formed by reaction of enantiomerically pure chiral bases such as brucine, quinine, ephedrine, strychnine, α-methyl-β-phenyl-ethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375–378). Enriched or purified enantiomers can be distinguished by methods used to distinguish other chiral molecules with asymmetric carbon atoms, such as optical rotation and circular dichroism.

EXAMPLES

The invention will be more fully understood by reference to the following examples. They should not, however, be construed as limiting the scope of the invention. All patent and literature citations are herein incorporated by reference in their entirety.

Example 1

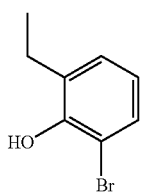

1

N-Bromosuccinimide (29.1 g, 163.7 mmol) was added as a suspension in CH$_2$Cl$_2$ (200 mL) over 2 h to a solution of 2-ethylphenol (20.0 gm, 163.7 mmol), diisopropylethylamine (2.3 mL, 16.4 mmol), and CH$_2$Cl$_2$ (300 mL). The resulting solution was maintained at room temperature for 2 h. One normal HCl (100 mL) was added and the mixture was stirred vigorously for 0.5 h. The layers were separated, and the organic phase was washed with 1 N HCl (2×100 mL). The combined aqueous layers were extracted with CH$_2$Cl$_2$ (1×100 mL), dried (Na$_2$SO$_4$), filtered, and concentrated. The residue was purified by silica gel chromatography (SiO$_2$, gradient elution 5 to 10% CH$_2$Cl$_2$/hexanes) to yield 26.5 g (80%) of 2-bromo-6-ethylphenol 1 as a yellow oil.

Example 2

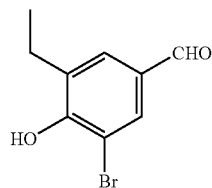

2

A solution of 2-bromo-6-ethylphenol 1 (3.8 g, 18.8 mmol) hexamethylene tetraamine (10.6 g, 75.4 mmol), and acetic acid (120 mL) was heated at reflux for 12 h. Most of the solvent was removed under reduced pressure, and the residue was poured into water (500 nL), and extracted with ethyl acetate (3×100 mL). The combined organic layers were washed with saturated aqueous NaHCO$_3$ until gas evolution ceased. The organic layer was washed with brine (1×100 mL), dried (Na$_2$SO$_4$), filtered, and concentrated. The residue was purified by silica gel chromatography (SiO$_2$, gradient elution 5 to 10% ethyl acetate/hexanes) to yield 2.0 g (46%) of 3-bromo-5-ethyl-4-hydroxybenzaldehyde 2 as a colorless solid.

Example 3

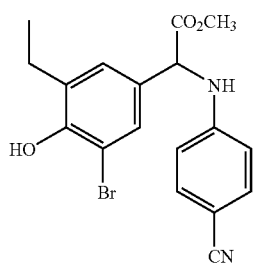

3

A solution of 3-bromo-5-ethyl-4-hydroxybenzaldehyde 2 (2.90 g, 12.6 mmol), 4-aminobenzonitrile (1.64 g, 13.9 mmol), and methanol (30 mL) was maintained at room temperature for 1 h. The solution was cooled to 0° C., and tosylmethylisocyanide (2.95 g, 15.2 mmol) and BF$_3$.Et$_2$O (5.70 mL, 45.4 mmol) were added sequentially. The mixture was allowed to warm to room temperature over 5 h, then water (1.13 mL, 63 mmol) was added and the mixture was stirred vigorously for 12 h. The solvent was removed under reduced pressure, and the residue was partitioned between ethyl acetate (200 mL) and saturated aqueous NaHCO$_3$ (200 mL). The aqueous layer was extracted with ethyl acetate (2×50 mL). The combined organic layers were washed with saturated aqueous NaHCO$_3$ (1×100 mL), brine (1×100 mL), dried (Na$_2$SO$_4$), and filtered. The solution was concentrated and adsorbed onto Celite®, then purified by silica gel chromatography (SiO$_2$, gradient elution 10–15–20% ethyl acetate/hexanes) to yield 3.8 g (77%) of methyl 2-(4-cyanophenylamino)-2-(3-bromo-5-ethyl-4-hydroxyphenyl) acetate 3 as a colorless solid.

Example 4

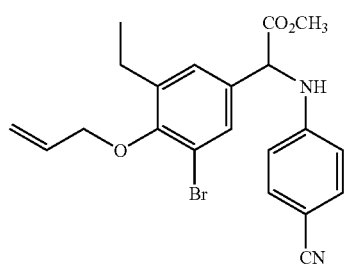

4

Allyl bromide (0.92 mL, 10.7 mmol) was added drop wise over 5 min to vigorously stirred mixture of 2-(4-cyanophenylamino)-2-(3-bromo-5-ethyl-4-hydroxyphenyl)acetate 3 (3.8 g, 9.76 mmol), Cs$_2$CO$_3$ (3.5 g, 10.74 mmol) and DMF (40 mL). The mixture was stirred vigorously for 4 h, then poured into ½-saturated NH$_4$Cl (400 mL). The mixture was extracted with Et$_2$O (3×100 mL). The combined organic layers were washed with water (3×50 mL), brine (1×100 mL), dried (MgSO$_4$), filtered, and concentrated. The residue was purified by silica gel chromatography (SiO$_2$, gradient elution 10–15–20% ethyl acetate/hexanes) to yield 3.4 g (81%) of methyl 2-(4-cyanophenylamino)-2-(4-(allyloxy)-3-bromo-5-ethylphenyl)acetate 4 as a colorless solid.

Example 5

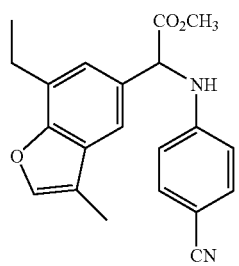

Following the general procedure of Larock et al (Tetrahedron Lett, 1988, 29:4687), a mixture of methyl 2-(4-cyanophenylamino)-2-(4-(allyloxy)-3-bromo-5-ethylphenyl)acetate 4 (5.00 g, 11.7 mmol), $Na_2CO_3$ (3.09 g, 29.1 mmol), $HCO_2Na$ (800 mg, 11.7 mmol), $Bu_4N^+C^-$ (3.56 g, 12.8 mmol) and DMA was degassed by bubbling $N_2$ for 1 h. Palladium(II) acetate (130 mg, 0.58 mmol) was added, the flask was sealed with a glass stopper and heated at 80° C. for 19 h. The mixture was poured into ½-saturated $NH_4Cl$ (500 mL) and extracted with diethylether ($Et_2O$, 4×125 mL). The combined organic layers were washed with saturated $NH_4Cl$ (1×125 mL), water (1×125 mL), brine (1×125 mL), dried over magnesium sulfate ($MgSO_4$), filtered, and concentrated. The residue was adsorbed onto Celite®, then purified by silica gel chromatography ($SiO_2$, gradient elution 10–15–20% ethyl acetate/hexanes) to yield 1.11 g (27%) of methyl 2-(4-cyanophenylamino)-2-(7-ethyl-3-methylbenzofuran-5-yl)acetate 5 as a colorless solid.

Example 6

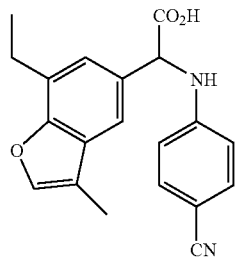

A mixture of methyl 2-(4-cyanophenylamino)-2-(7-ethyl-3-methylbenzofuran-5-yl)acetate 5 (1.11 g, 3.18 mmol), $LiOH \cdot H_2O$ (700 mg, 15.9 mmol), THF (10 mL) and water (5 ml) was stirred vigorously for 3 h. The mixture was partitioned between 1N HCl (100 ml) and ethyl acetate (100 ml). The aqueous layer was extracted with ethyl acetate (3×50 mL). The combined organic layers were washed with brine (1×125 mL), dried ($MgSO_4$), filtered, and concentrated to yield 1.09 g (98%) of 2-(4-cyanophenylamino)-2-(7-ethyl-3-methylbenzofuran-5-yl)acetic acid 6 as an off-white solid.

Example 7

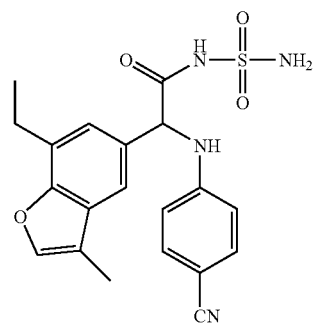

2-(4-Cyanophenylamino)-2-(7-ethyl-3-methylbenzofuran-5-yl)acetic acid 6 (5.45 g, 16.4 mmoles), carbonyldiimidazole (CDI, 5.28 g 32.6 mmoles) were combined under a nitrogen atmosphere and THF (50 ml) added. The reaction was stirred for 1 h. Sulfamide (4.7 g, 49 mmoles) was added to the reaction followed by drop wise addition of 1,8-diazabiocyclo[5.4.0]undec-7-ene (DBU, 7.3 ml, 49 mmoles). The reaction was then stirred an additional 2 hours at room temperature and the solvent removed in vacuo. The residue was taken up in ethyl acetate (ca. 150 ml) and washed with aqueous 2 N HCl. The organic layer was dried over anhydrous sodium sulfate, filtered and concentrated to a yellow foam. The crude product was then purified on a silica flash column eluted with 40% ethyl acetate/60% hexane to provide 2-(4-cyanophenylamino)-2-(7-ethyl-3-methylbenzofuran-5-yl)acetylsulfamide 7 (4.7 g).

Example 8

2-(4-Cyanophenylamino)-2-(7-ethyl-3-methylbenzofuran-5-yl)acetylsulfamide 7 (1 gm) was dissolved 4 ml dry ethanol and cooled to 0° C. with an ice bath. HCl saturated ethanol (30 ml) was added and the reaction stirred at 0° C. for 6 h. The solvent was removed in vacuo and replaced with 2N ammonia in methanol (50 ml). The reaction was stirred for 48 hours and the solvent removed in vacuo. The crude product was purified by reverse-phase chromatography (acetonitrile:water:0.1% TFA) to provide purified 2-(4-acetamidinephenylamino)-2-(7-ethyl-3-methylbenzofuran-5-yl) acetylsulfamide 8. Racemic 8 could be separated into its individual enantiomers using a S-Welko chiral column and eluted with isopropyl alcohol/water buffered at pH=5.5. The individual enantiomers were then purified once more on the reverse-phase column with water/acetonitrile with 0.1% TFA.

Example 9

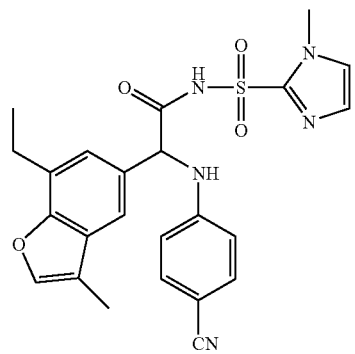

Carboxylic acid 6 (1.69 gm, 5 mmoles), carbonyl diimidazole (1.6 gm, 10 mmoles) were combined under a nitrogen atmosphere and THF (17 ml) added. The reaction was stirred for 1 h. 1-methylimidazole-4-sulfonamide (1.6 g, 10 mmoles) was added to the reaction followed by drop wise addition of 1,8-diazabiocylco[5.4.0]undec-7ene (DBU, 3 ml, 20 mmoles). The reaction was then stirred an additional 2 hours at room temperature and the solvent removed in vacuo. The crude product was then purified on a silica flash column eluted with 40% ethyl acetate/60% hexane to provide 2-(4-cyanophenylamino)-2-(7-ethyl-3-methylbenzofuran-5-yl)acetylsulfonamido 2-(1-methyl)imidazole 9 (1.17 g).

Example 10

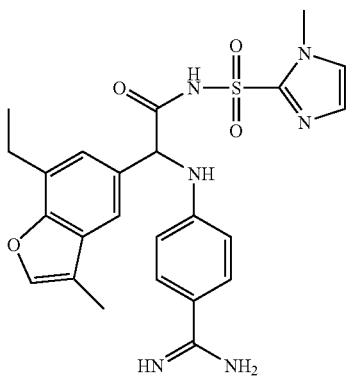

2-(4-Cyanophenylamino)-2-(7-ethyl-3-methylbenzofuran-5-yl)acetylsulfonamido 2-(1-methyl)imidazole 9 (269 mg) was dissolved 4 ml dry ethanol HCl-saturated ethanol (30 ml) was added and the reaction stirred at 0° C. for 6 h. The solvent was removed in vacuo and replaced with 2N ammonia in methanol (50 ml). The reaction was stirred for 48 hours and the solvent removed in vacuo. The crude product was purified by reverse-phase chromatography (acetonitrile: water: 0.1% TFA) to provide 2-(4-acetamidinephenylamino)-2-(7-ethyl-3-methylbenzofuran-5-yl)acetylsulfonamido 2-(1-methyl)imidazole 23. Racemic 23 could be separated into its individual enantiomers using a S-Welko chiral column and eluted with isopropyl alcohol/water buffered at pH 5.5. The individual enantiomers were then purified once more on the reverse-phase column with water/acetonitrile with 0.1% TFA.

Example 11

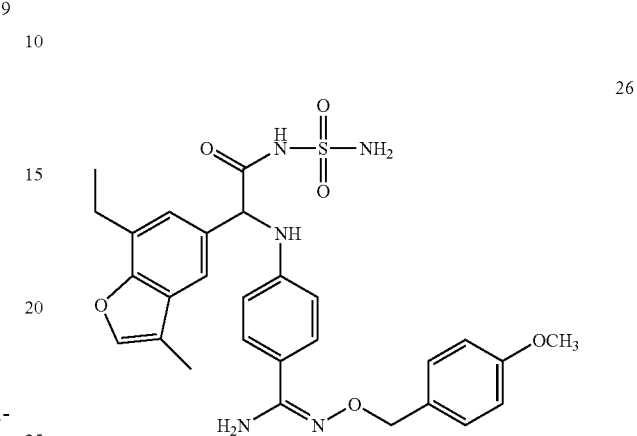

2-(4-Cyanophenylamino)-2-(7-ethyl-3-methylbenzofuran-5-yl)acetylsulfamide 7 (1 gm) was dissolved 4 ml dry ethanol and cooled to 0° C. with an ice bath. HCl-saturated ethanol (30 ml) was added and the reaction stirred at 0° C. for 6 h. The solvent was removed in vacuo and replaced with 0-(4-methoxybenzyl) hydroxylamine (0.5 g) in methanol (50 ml). Diisopropylethylamine (iPr₂NEt, 5 ml) was added. The reaction was stirred for 48 hours and the solvent removed in vacuo. The crude product was purified by reverse-phase chromatography (acetonitrile: 0.1% TFA) to provide the purified O-para-methoxybenzyloxime acetylsulfamide product 26. Racemic 26 could be separated into its individual enantiomers using a S-Welko chiral column and eluted with isopropyl alcohol/water buffered at pH 5.5. The individual enantiomers were then purified once more on the reverse-phase column with water/acetonitrile with 0.1% TFA. Compound 26 as an amorphous solid had a solubility in water of 115 μM at pH 2, and 98 μM at pH 6.5

Example 12

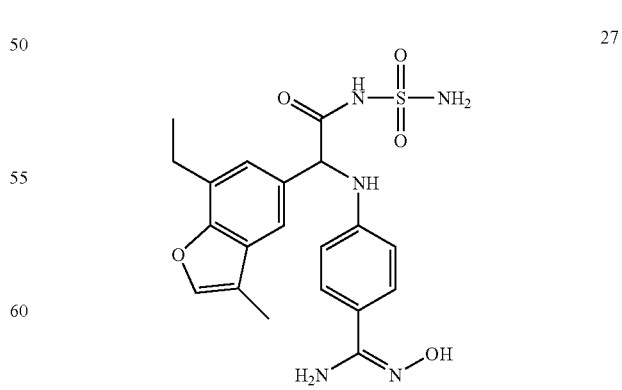

2-(4-Cyanophenylamino)-2-(7-ethyl-3-methylbenzofuran-5-yl)acetylsulfamide 7 (630 mg) was dissolved 4 ml dry ethanol and cooled to 0° C. with an ice bath. HCl-Saturated ethanol (30 ml) was added and the reaction stirred at 0° C. for 6 h. The solvent was removed in vacuo and replaced with hydroxylamine (0.526 mg) in methanol (50 ml). Diisopropylethyl amine (2.7 ml) was added. The reaction was stirred for 48 hours and the solvent removed in vacuo. The crude product was purified by reverse-phase chromatography (acetonitrile: water: 0.1% TFA) to provide the purified oxime acetylsulfamide product 27.

Example 13

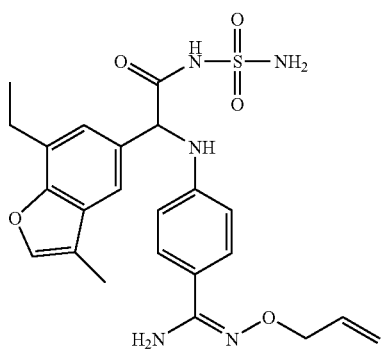

2-(4-Cyanophenylamino)-2-(7-ethyl-3-methylbenzofuran-5-yl)acetylsulfamide 7 (1 gm) was dissolved 4 ml dry ethanol and cooled to 0° C. with an ice bath. HCl-Saturated ethanol (30 ml) was added and the reaction stirred at 0° C. for 6 h. The solvent was removed in vacuo and replaced with O-allylhydroxylamine (0.530 mg) in methanol (50 ml). Diisopropylethyl amine (2.7 ml) was added. The reaction was stirred for 48 hours and the solvent removed in vacuo. The crude product was purified by reverse-phase chromatography (acetonitrile: water: 0.1% TFA) to provide the purified O-allyl oxime acetylsulfamide product 28. Racemic 28 could be separated into its individual enantiomers using a S-Welko chiral column and eluted with isopropyl alcohol/water buffered at pH=5.5. The individual enantiomers were then purified once more on the reverse-phase column with water/acetonitrile with 0.1% TFA.

Example 14

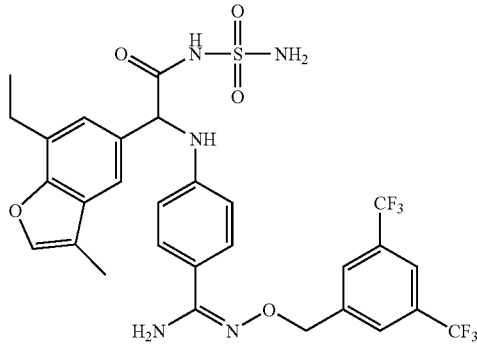

2-(4-Cyanophenylamino)-2-(7-ethyl-3-methylbenzofuran-5-yl)acetylsulfamide 7 (1 gm) was dissolved 4 ml dry ethanol and cooled to 0° C. with an ice bath. HCl saturated ethanol (30 ml) was added and the reaction stirred at 0° C. for 6 h. The solvent was removed in vacuo and replaced with O-(bis 3,5 trifluoromethylbenzyl)hydroxylamine (1.25 g) in methanol (50 ml). Diisopropylethyl amine (2.1 ml) was added. The reaction was stirred for 48 hours and the solvent removed in vacuo. The crude product was purified by reverse-phase chromatography (acetonitrile:water:0.1% TFA) to provide the purified O-(3,5bis-trifluoromethyl)benzyloxime acetylsulfamide product 29.

Example 15

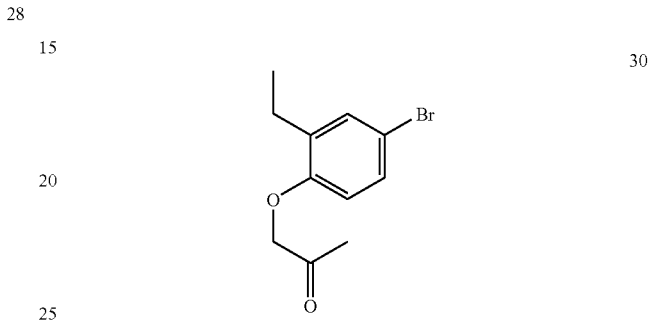

4-bromo-2-ethylphenol (72.79 g, 362 mmoles) was dissolved in acetone (1.3 liter) and potassium carbonate (100 g, 724 mmoles) was added. The reaction was stirred for five minutes. Chloroacetone (43.2 ml, 543 mmoles) and sodium iodide (13.6, 90 mmoles) was added and the reaction turned orange upon stirring. The reaction was stirred overnight at room temperature and the solvent removed in vacuo. Ethyl acetate (2.5 l) and water (800 ml) were added. The organic layer was separated, washed with aqueous $Na_2S_2O_3$, dried over sodium sulfate and filtered. The solvent was removed in vacuo and the crude product run through a plug of silica gel (ca. 500 g) and eluted with 20% ethyl acetate in hexane. The solvent was removed to obtain 95 g of 1-(4-bromo-2-ethylphenoxy)propan-2-one 30.

Example 16

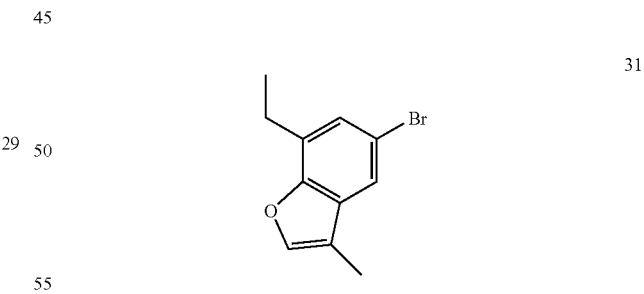

A stirred solution of polyphosphoric acid (461 ml) was heated to 95° C., and 1-(4-bromo-2-ethylphenoxy)propan-2-one 30 (93 gm) was added portionwise. The reaction was stirred 1 hour. The reaction was determined to be complete and the contents poured onto 1:1 hexane; 10% aqeous sodium hydroxide (2 liters). A strong exotherm was noted. The organic layer was separated and washed twice with 1 N $Na_2S_2O_3$. The organic layer was then stirred with charcoal and anhydrous magnesium sulfate for 30 minutes. The reaction was filtered through celite and the solvent removed in vacuo. The crude product was run through a plug of silica gel (375 g) and eluted with hexanes. The solvent was removed in vacuo to yield 67.58 g of 5-bromo-7-ethyl-3-methylbenzofuran 31.

Example 17

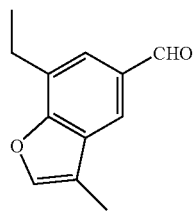

32

5-Bromo-7-ethyl-3-methylbenzofuran 31 (21.25 g, 89 mmoles) was dissolved in dry THF (470 ml) and cooled to −78° C. under a nitrogen atmosphere. Sec-butyl lithium (69.8 ml of a 1.4 M solution, 98 mmoles) was added drop wise to the cooled reaction. The reaction mixture turned a reddish color. Dimethylformamide (51.6 ml, 666 mmoles) was added to the reaction at −78° C. The reaction was allowed to warm to room temperature and stirred overnight. The reaction was poured into 800 ml of ice/ethyl acetate and the organic layer separated. The aqueous layer was washed with ethyl acetate and the combined organic layer washed with water. The solution was dried over sodium sulfate, filtered, and the solvent removed in vacuo. The crude product was purified by flash chromatography (750 g silica, 8% ethyl acetate in hexanes) to yield 7.02 g of 7-ethyl-3-methylbenzofuran-5-carbaldehyde 32.

Example 18

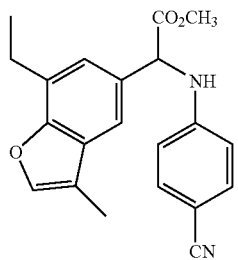

5

7-Ethyl-3-methylbenzofuran-5-carbaldehyde 32 (2 g, 10.9 mmole), dry methanol (40 ml), and 4-aminobenzonitrile (1.42 g, 12 mmoles) were combined and heated to reflux under a nitrogen atmosphere. The reaction was refluxed for 2.5 hours and then cooled to room temperature. Tosylmethylisonitrile (2.12 g, 10.0 mmoles) was added with 9 ml methanol. The reaction mixture was cooled to 0° C. and BF3-OEt2 was added drop wise over 40 minutes. The reaction was allowed to stir for 2 hours and water (2 ml) was added and the reaction stirred for at least 1 hour. The solvent was removed in vacuo and the residue partitioned between ethyl acetate and aqueous citric acid. The organic layer was separated, washed with brine, dried over sodium sulfate and the solvent removed in vacuo. The crude product was purified by flash chromatography (25% ethyl acetate in hexanes) to yield 2.19 g of methyl 2-(4-cyanophenylamino)-2-(7-ethyl-3-methylbenzofuran-5-yl)acetate 5.

Example 19

Tissue Factor/Factor VIIa Antagonist Assay

This procedure can be used to determine the constant of inhibition (Ki) for a sample compound of the invention.

Materials:

Assay Buffer: 100 mM Hepes pH 7.8, 140 mM NaCl, 0.1% PEG-8000, 0.02% Tween-80, 5 mM CaCl$_2$ Coagulation Factor: recombinant human factor VIIa (NB #25942–16)

Cofactor: soluble Tissue Factor (1-219)

Substrate: Chromozym-tPA (Boehringer Mannheim, Cat. #1093 037) Reconstitute at 20 mM in H$_2$O. Dilute to 4 mM in assay buffer with CaCl$_2$ prior to use.

Samples: Dilute samples to 3% DMSO in assay buffer (lacking CaCl$_2$).

Procedure:

1. Prepare a solution of 2 μg/mL (90 nM) tissue factor and 1.5 μg/mL (30 nM) factor VIIa in assay buffer with CaCl$_2$.
2. Incubate for 15 minutes at room temperature.
3. Add 50 μL sample to each well.
4. Add 50 μL tissue factor/factor VIIa solution to each well.
5. Incubate for 15 minutes at room temperature with gentle agitation.
6. Add 50 μL substrate to each well.
7. Agitate plate for 20–25 sec.
8. Monitor absorbance at 405 nM every 10 sec for a total of 5 minutes at room temperature.
9. Calculate Vmax over 10 points.

Example 20

Factor Xa, Thrombin, and Plasma Kallikrein Assays

These procedures can be used to determine the constant of inhibition (Ki) for a sample compound of the invention.

Materials:

Assay Buffer: 100 mM Hepes pH 7.8, 140 mM NaCl, 0.1% PEG-8000, 0.02% Tween-80

Coagulation human Factor Xa, Thrombin, or Plasma Kallikrein (Hematologic Technologies)

Factor: Dilute to 0.45 μg/mL (9.8 nM) in assay buffer.

Substrate: S-2222, S2366 or S2302—(See below—Chromogenix Inc,) Reconstitute at 5 mM in H$_2$O. Dilute to 1.5 mM in assay buffer prior to use.

Samples: Dilute samples to 3% DMSO in assay buffer.

Procedure:

1. Add 50 μL sample to each well.
2. Add 50 μL appropriately diluted coagulation factor to each well.
3. Incubate for 5 minutes at room temperature with gentle agitation.
4. Add 50 μL appropriately diluted substrate to each well.
5. Agitate plate for 20–25 sec.
6. Monitor absorbance at 405 nM every 10 sec for a total of 5 minutes at room temperature.
7. Calculate Vmax over 10 points.

Assay—Enzyme, Substrate and Final Concentrations

| Assay | TF/FVIIa | FXa | Thrombin | PlasmaKallikrein |
|---|---|---|---|---|
| Coag Factor Final concentration | 10 nM FVIIa 30 nM TF | 3.3 nM | 8.2 nM | 1.5 nM |
| Substrate | Chromozyme tPA | S-2222 | S-2366 | S-2302 |
| Final Conc. of Substrate | 1.33 mM | 0.5 mM | 0.3 mM | 0.3 mM |

Example 21

Pharmacokinetic Assays

Permeability—Caco-2 or MDCK cells were maintained in Dulbecco's Modified Eagle Medium supplemented with 10% FBS, 1% penicillin/streptomycin, 1% L-glutamine, and 1% MEM non-essential amino acids solution. Cells were cultured at 37° C. in an atmosphere of 5% $CO_2$ and 95% relative humidity. Cells were passaged at 80–90% confluency using Trypsin-EDTA solution. Cells were seeded on polycarbonate Transwell® filters pre-coated with rat-tail collagen. The pore size was 0.4 µm with a growth area of 1 $cm^2$ and cells were seeded at a density of $16 \times 10^4$ cells/mL or $10 \times 10^4$ cells/mL (Caco-2 and MDCK respectively). Monolayers were rinsed with Hanks Balanced Salt Solution (HBSS) prior to starting the assay. Transport assay donor solutions were 200 µM in HBSS at pH 5.5, 6.5 or 7.4.1% DMSO or 1% Captisol was added as a solubilizing agent if necessary. Cells were incubated in a shaking water bath (35 rpm). 200 µL samples were taken from the receiver side at 0, 1.5 and 3 hours. Samples were also taken from the donor side at 0 and 3 hours. Cell layer integrity was monitored with lucifer yellow ($<1 \times 10^{-6}$ cm/sec). Lucifer yellow samples were analyzed on a CytoFluor® multi-well plate reader, Series 4000 (excitation 1:485, emission 1:530). All other samples were analyzed on an Agilent 1100 HPLC system using RP-HPLC and a Phenomenex C18 Luna 3 µm particle column, 50×2.0 mm. Mobile phases were 0.1%

FA in H20 and 0.1% TFA in Acetonitrile. Clearance and Half Life

Jugular Vein Cannulation—Animals are anesthetized via IP injection using Ketamine/Xylazine/saline solution (@ 0.25 mL/kg). Animals are weighed prior to dosing of anesthetic to determine proper dosage. Sterile instruments and aseptic technique are used throughout surgery. This includes wearing a mask, clean lab coat or scrubs and sterile gloves. The ventral and dorsal neck areas are shaved and prepped with betadine and alcohol. A small skin incision is made over the jugular vein. Using blunt dissection techniques, free the intended vessel from surrounding tissue and thread two sutures under the vein. Tie the cranial suture, nick the vessel, insert the catheter, and use the distal suture to secure the catheter. Dissect a subcutaneous passage between the catheter insertion point and the intrascapular space; make a small exit hole at the nape of the neck. Then, using hemastats, pull the cannula through the passage to the dorsal neck area. Confirm that the cannula is still properly placed, flush with appropriate heparin/saline solution, and knot the distal end of the cannula. Place a suture tie around the knot, coil the cannula under the skin and close the dorsal incision, leaving the "tie" slightly exposed for ease of externalizing the catheter. Close the ventral incision. The animal should be recovered on a circulating heating blanket or equivalent and returned to its room when it's able to right itself.

Test Articles

Compounds are formulated with polyethylene glycol 400 (PEG) at 30% (IV) or 60% (PO).

Dose Administration

Intravenous (IV) dosing is accomplished with a bolus injection into a lateral tail vein. Animals are restrained using a rat restrainer to minimize mis-dosings and to reduce animal stress. Individual doses are calculated based on body weights taken the morning of the dose.

Oral (PO) dosing is accomplished by oral gavage using a 3½ inch stainless steel animal feeding tube. Animals are restrained by grasping gently with our hands to reduce animal stress. Individual doses are calculated based on body weights taken the morning of the dose.

Blood sample Collection

Blood (approximately 0.2 mL) is collected from an jugular cannula. For occasions when the jugular cannula fails, blood is removed from the remaining lateral tail vein. The whole blood was placed into Microtainer® tubes containing $K_2EDTA$ anticoagulant. Samples are inverted several times to ensure proper mixing with anticoagulant and are stored on ice until centrifugation. Samples are centrifuged at 10,000×g for 5 minutes and plasma is transferred to 1.5 mL microcentrifuge tube. Blood samples, for IV dose administrations are collected prior to the dose administration (predose) and at 2, 5, 10, 20, 30, 45, 60, 120 minutes, 4, 6, 8 and 10 hours postdose of the dose administration. For PO dose administration, the blood collection time points are the same as IV dose administration, except no blood sample is collected at 2 minutes.

All plasma samples are measured by LC/MS/MS. All pharmacokinetic parameters, clearance (CL), half life (t1/2), area under curve (AUC) and maximum conc. (Cmax) are determined using WinNonin (version 3.2).

Example 22

Dosing of Benzofuran Compounds in Rhesus Monkeys

IV Bolus: Inhibitors were formulated in a 1 mg/ml solution of 20–30% PEG 400/sterile water. The drug was administered as an IV bolus over 1 minute at 1 mg/kg. 1.0 ml blood samples were collected at each time point on 20 µl 8.5% $K_2EDTA$. Blood samples for the IV dosed animals were be collected from a short, large bore catheter (needle <25G) placed in the saphenous or cephalic vein for all time points up to 3 hours after dosing. The catheters were then removed, the animals returned to their cages and latter samples collected by venipuncture. Venipuncture samples can be obtained from any superficial vein that can easily be compressed (e.g. cephalic, or saphenous but not from the femoral plexus). Sample time points were taken generally at the following times: pre-dose, 2, 5, 10, 20, 30, 40, 60, 90, 120, 150, 180 minutes and at 4, 6, 12, 24, and 48 hours. See FIGS. 1 and 2.

Oral (PO): Inhibitors were formulated in a 1 mg/ml solution of 20–30% PEG 400/sterile water. The drug was administered at 2 mg/kg via a nasogastric tube and the tube flushed with 10 ml water after dosing. All blood samples following oral dosing were obtained by venipuncture. Venipuncture samples can be obtained from any superficial vein that can easily be compressed (e.g. cephalic, or saphenous but not from the femoral plexus). Sample time points were taken generally at the following times: pre-dose, 0.5, 1, 2, 3, 4, 6, 8, 10, 12, 24 36 and 48 hours. See FIG. 3.

We claim:

1. A compound of formula I:

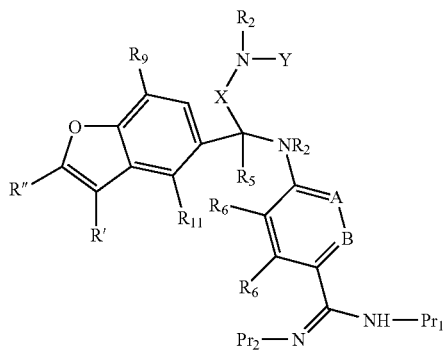

wherein

A and B are independently CH, or $CR_3$;

X is C=O or $(CR_{4a}R_{4b})_m$ where m is 1 or 2;

Y is $S(O)_n$—$R_1$, $S(O)_n$—$NR_2R_2$, $S(O)_n$—$OR_2$, $C(O)R_1$, $C(S)R_1$, $C(O)$—$OR_1$, or $C(O)$—$NR_2R_2$, where n is 1 or 2;

$Pr_1$ is hydroxy, alkyl, alkoxy, alkanoyl, alkanoyloxy, alkoxycarbonyl, aryloxy, or arylalkoxy;

$Pr_2$ is H, hydroxy, alkyl, alkoxy, alkanoyl, alkanoyloxy, alkoxycarbonyl, aryloxy, or arylalkoxy;

said alkyl, alkoxy, alkanoyl, alkanoyloxy, alkoxycarbonyl, aryloxy or arylalkoxy are independently and optionally substituted with hydroxy, halogen, carboxyl, alkyl, halosubstituted alkyl, alkoxy, or a carbocycle optionally substituted with 1–5 hydroxy, alkoxy, carboxyl, alkyl, or halosubstituted alkyl; and one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—;

R' and R" are each independently H, carboxyl, alkyl, alkoxy, alkanoyl, alkanoyloxy or alkoxycarbonyl; wherein said alkyl, alkoxy, alkanoyl, alkanoyloxy and alkoxycarbonyl groups are optionally substituted with amino, hydroxy, alkoxy, acyl, acyloxy, or a substituted or unsubstituted carbocycle; and one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—;

$R_1$ is $C_1$–$C_6$ alkyl, $C_2$–$C_6$ alkenyl, $C_2$–$C_6$ alkynyl, $C_3$–$C_6$ cycloalkyl, phenyl, naphthyl, or benzyl; and $R_1$ is optionally substituted with 1–3 substituents selected from the group consisting of halo, nitro, $C_1$–$C_6$ alkyl, $NR_7R_8$, $OR_7$, $SR_7$, $C_1$–$C_6$ alkyl-$C(O)OR_7$, $C_1$–$C_6$ alkyl-$OC(O)R_7$, $C_1$–$C_6$ alkyl-$C(O)R_7$, $C_1$–$C_6$ alkyl-$OR_7$, $C_1$–$C_6$ haloalkyl $C_1$–$C_6$ alkyl-$NR_7R_8$, $C(Q)OR_7$, $OC(O)R_7$, $C(O)NR_7R_8$, $OC(O)NR_7R_8$, $NHC(O)R_7$, and $NHC(O)NR_7R_8$;

each $R_2$ is, independently, H, alkyl, substituted alkyl, aryl, substituted aryl, $C(O)R_7$ or $C(NH)R_7$, or the two $NR_2$ and $NR_2$ groups together form a heterocycle;

$R_3$ is H, $C_1$–$C_6$ alkyl, $C_1$–$C_6$ alkoxy, halogen or OH;

$R_{4a}$ and $R_5$ are independently a member selected from the group consisting of H, unsubstituted or substituted alkyl, unsubstituted or substituted alkoxyalkyl, unsubstituted or substituted haloalkyl, unsubstituted or substituted aryl, alkyl-$OR_7$, alkyl-$NR_7R_8$, alkyl-$OC(O)R_7$, alkyl-$C(O)OR_7$, alkyl-$C(O)R_7$, $OC(O)R_7$, $C(O)OR_7$, $C(O)R_7$ and members in which the alkyl, $R_7$ or $R_8$ is substituted with 1–3 F, Cl, Br, I, $OR_7$, $SR_7$, $NR_7R_8$, $OC(OR_7)$, $C(O)OR_7$, $C(O)R_7$, $C(O)NR_7R_8$, NHC(NH)$NH_2$, $PO_3$;

$R_{4b}$ is H, alkyl, or substituted alkyl;

$R_6$ is selected from the group selected from H, $C_1$–$C_6$ alkyl, $C_1$–$C_6$ alkyl-$OR_7$, $C_1$–$C_6$ alkyl-N $R_7R_8$, $C_1$–$C_6$ haloalkyl, halo, cyano, $OR_7$, $SR_7$, $NR_7R_8$, $C(O)OR_7$, $C(O)R_7$ and $OC(O)R_7$;

$R_7$ and $R_8$ are independently H or $C_1$–$C_6$ alkyl;

$R_9$ is H, halogen, hydroxy, alkyl, alkoxy, alkanoyl, $NR_7R_8$ or $SR_7$; wherein said alkyl, alkoxy, and alkanoyl are optionally substituted with halogen, amino, hydroxy, carboxyl, alkoxy or alkoxycarbonyl;

$R_{11}$ is selected from the group consisting of H, halo, nitro, cyano, $C_1$–$C_6$ alkyl, $C_6$–$C_{10}$ aryl, $NR_7R_8$, $OR_7$, $SR_7$, $C_1$–$C_6$ alkyl-$C(O)R_7$, $C_1$–$C_6$ alkyl-$C(O)NR_7R_8$, $C_1$–$C_6$ alkyl-$C(O)OR_7$, $C_1$–$C_6$ alkyl-$OC(O)R_7$, $C_1$–$C_6$ alkyl-$OR_7$, $OC_1$–$C_6$ alkyl-$C(O)R_7$, $OC_1$–$C_6$ alkyl-$C(O)OR_7$, $OC_1$–$C_6$ alkyl-$OC(O)R_7$, O—$C_1$–$C_6$ alkyl-$OR_7$, $OC_1$–$C_6$ alkyl-$C(O)NR_7R_8$, $C_1$–$C_6$ haloalkyl, $OR_{12}$, $C_1$–$C_6$ alkyl-$R_{12}$, O—$C_1$–$C_6$ alkyl-$R_{12}$, $C(O)R_7$, $C(O)OR_{12}$, $C(O)NR_7R_8$, $OC(O)NR_7R_8$, $NR_7C(O)R_7$, $NR_7C(O)R_{12}$, $NR_7C(O)$—$NR_7R_8$, $NR_7$—($C_1$–$C_6$ alkyl)-$C(O)$—$NR_7R_8$, $NR_7C(O)OR_7$, $NR_7C(O)OR_{12}$, $NR_7S(O)_n$—$R_1$, $NR_7S(O)_n$—$R_7$ and $NR_7S(O)_n$—$R_{12}$, wherein $R_{12}$ is unsubstituted or substituted $C_6$–$C_{10}$ aryl and n is 1 or 2; and acid and base addition salts thereof.

2. The compound of claim 1 wherein $R_9$ is H, halogen alkyl, alkoxy, halo, nitro, cyano, wherein said alkyl and alkoxy are optionally substituted with hydroxy, halogen, alkoxy, aryl and aryloxy; and $R_{11}$ is H.

3. The compound of claim 2 wherein $R_9$ is H, methoxy, ethoxy, ethyl, propyl, ethynyl, Cl, I, propyn-1-yl or 1-chlorovinyl.

4. The compound of claim 3 wherein $R_9$ is ethyl.

5. The compound of claim 1 wherein R' is H, halogen alkyl, alkoxy, halo, nitro, cyano, wherein said alkyl and alkoxy are optionally substituted with hydroxy, halogen, alkoxy, aryl and aryloxy; and $R_{11}$ is H.

6. The compound of claim 5 wherein R' is Cl, methyl, ethyl, propyl, hydroxyethyl or benzoyloxyethyl.

7. The compound of claim 6 wherein R' is methyl.

8. The compound of claim 1 wherein R" is alkyl, optionally substituted with amino, hydroxy, alkoxy, acyl, acyloxy, or a carbocycle; alkanoyl, alkoxycarbonyloxyalkyl, alkanoyloxyalkyl, or acyloxyalkyl; wherein said carbocycle is optionally substituted with halogen, haloalkyl, alkoxy or carboxyl.

9. The compound of claim 8 wherein R" is ethyl, propyl, t-butyl, hydroxymethyl, hydroxyethyl, 1-methoxy-1-methylethyl, 1-hydroxy-1-methylethyl, methoxymethyl, aminomethyl, N-dimethylaminomethyl, N-acetylaminomethyl, N-acetyl-N-methylaminomethyl, acetylethyl, propanoyl, acetyl, ethyloxycarbonyloxyemethyl, acetyloxyethyl, t-butylcarbonyloxyethyl, benzoyloxyethyl, 3,5-diCF$_3$-benzoyloxyethyl, trichloroacetyloxyethyl, or propanoyloxyethyl.

10. The compound of claim 1 wherein R" is H.

11. The compound of claim 1 wherein Y is $S(O)_n$—$NR_2R_2$ wherein both $R_2$ are H or alkyl.

12. The compound of claim 11 wherein both $R_2$ substituents are H.

13. The compound of claim 1 wherein X is a carbonyl group.

14. The compound of claim 1 wherein Y is $S(O)_n$—$R_1$ where n is 2; and $R_1$ is selected from the group consisting of $C_1$–$C_6$ alkyl, $C_2$–$C_6$ alkenyl, $C_2$–$C_6$ alkynyl, $C_3$–$C_6$ cycloalkyl, phenyl, naphthyl, and benzyl and $R_1$ optionally substituted with 1–3 substituents selected from the group consisting of halo, nitro, $C_1$–$C_6$ alkyl, $NR_7R_8$, $OR_7$, $SR_7$, $C_1$–$C_6$ alkyl-C(O)$OR_7$, $C_1$–$C_6$ alkyl-OC(O)$R_7$, $C_1$–$C_6$ alkyl-C(O)$R_7$, $C_1$–$C_6$ alkyl-$OR_7$, $C_1$–$C_6$ haloalkyl, $C_1$–$C_6$ alkyl-$NR_7R_8$, C(O)$OR_7$, OC(O)$R_7$, C(O)$NR_7R_8$, OC(O)$NR_7R_8$, NHC(O)$R_7$, and NHC(O)$NR_7R_8$, where $R_7$ and $R_8$ independently are H or $C_1$–$C_6$ alkyl.

15. The compound of claim 1 wherein A and B are both CH.

16. The compound of claim 1 wherein both $R_6$ are H.

17. The compound of claim 1 selected from:

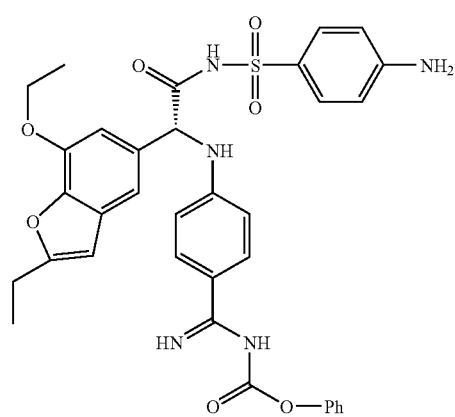

18

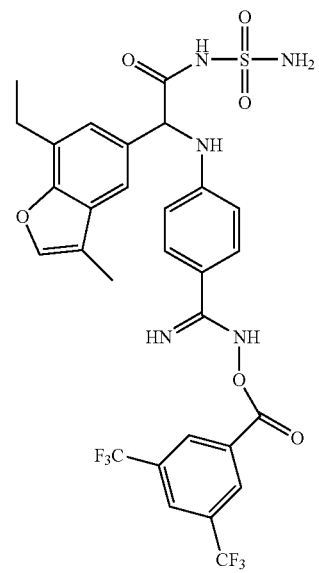

20

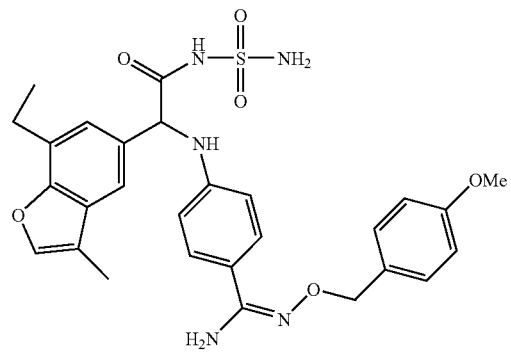

26

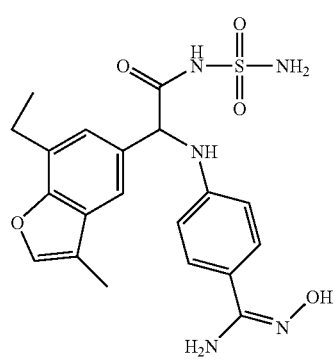

27

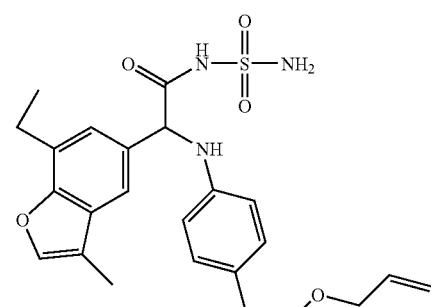

28

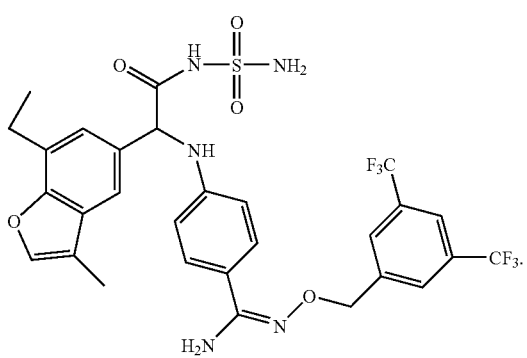

and

29

18. The compound of claims 1 wherein $Pr_1$ is hydroxy, alkoxy, alkanoyl, aryloxy or aryl; wherein said alkoxy, alkanoyl, aryloxy and aryl are optionally substituted with halogen; and $Pr_2$ is H.

19. The compound of claim 1 having the formula:

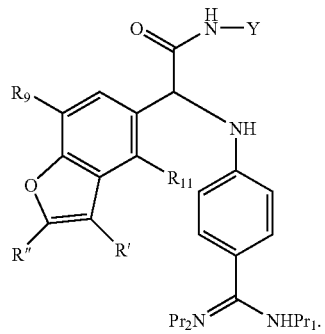

20. The compound of claim 19 having the formula:

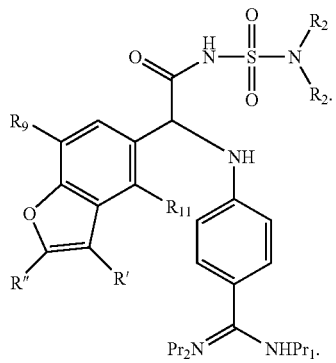

21. The compound of claim 20 wherein $R_2$ is independently H or $C_1$–$C_6$ alkyl, and $R_{11}$ is H.

22. The compound of claim 21 wherein R', R", $R_9$ are independently H or $C_1$–$C_6$ alkyl, and $Pr_1$ and $Pr_2$ are H.

23. The compound of claim 21 wherein R', R", $R_9$ are independently H or $C_1$–$C_6$ alkyl; $Pr_1$ is H; and $Pr_2$ is hydroxy, $C_1$–$C_6$ alkyl, $C_1$–$C_6$ alkoxy, $C_1$–$C_1$–$C_6$ alkanoyl, $C_1$–$C_6$ alkanoyloxy, $C_1$–$C_6$ alkoxycarbonyl, aryloxy, or arylalkoxy.

24. The compound of claim 21 wherein $Pr_2$ is benzyloxy (OBn) or substituted benzyloxy.

25. A compound of formula I:

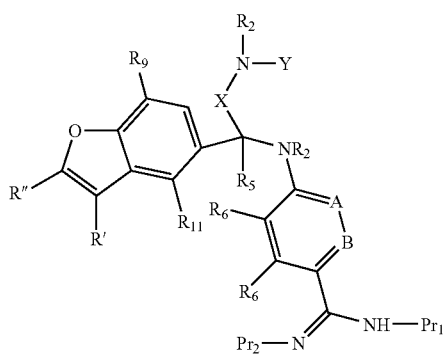

wherein
A and B are CH;
X is C=O;
Y is $S(O)_2$—$R_1$, $S(O)_2$—$NR_2R_2$, or $S(O)_2$—$OR_2$;
$Pr_1$ and $Pr_2$ are H;
R' and R" are each independently H, carboxyl, alkyl, alkoxy, alkanoyl, alkanoyloxy or alkoxycarbonyl; wherein said alkyl, alkoxy, alkanoyl, alkanoyloxy and alkoxycarbonyl groups are optionally substituted with amino, hydroxy, alkoxy, acyl, acyloxy, or a substituted or unsubstituted carbocycle; and one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—;

$R_1$ is $C_1$–$C_6$ alkyl, $C_2$–$C_6$ alkenyl, $C_2$–$C_6$ alkynyl, $C_3$–$C_6$ cycloalkyl, phenyl, naphthyl, or benzyl; and $R_1$ is optionally substituted with 1–3 substituents selected from the group consisting of halo, nitro, $C_1$–$C_6$ alkyl, $NR_7R_8$, $OR_7$, $SR_7$, $C_1$–$C_6$ alkyl-C(O)$OR_7$, $C_1$–$C_6$ alkyl-OC(O)$R_7$, $C_1$–$C_6$ alkyl-C(O)$R_7$, $C_1$–$C_6$ alkyl-$OR_7$, $C_1$–$C_6$ haloalkyl $C_1$–$C_6$ alkyl-$NR_7R_8$, C(O)$OR_7$, OC(O)$R_7$, C(O)$NR_7R_8$, OC(O)$NR_7R_8$, NHC(O)$R_7$, and NHC(O)$NR_7R_8$;

each $R_2$ is, independently, H, alkyl, substituted alkyl, aryl, substituted aryl, C(O)$R_7$ or C(NH)$R_7$, or the two $NR_2$ and $NR_2$ groups together form a heterocycle;

$R_3$ is H, $C_1$–$C_6$ alkyl, $C_1$–$C_6$ alkoxy, halogen or OH;
$R_5$ is H;
$R_6$ is H;
$R_7$ and $R_8$ are independently H or $C_1$–$C_6$ alkyl;
$R_9$ is H, halogen, hydroxy, alkyl, alkoxy, alkanoyl, $NR_7R_8$ or $SR_7$; wherein said alkyl, alkoxy, and alkanoyl are optionally substituted with halogen, amino, hydroxy, carboxyl, alkoxy or alkoxycarbonyl;

$R_{11}$ is selected from the group consisting of H, halo, nitro, cyano, $C_1$–$C_6$ alkyl, $C_6$–$C_{10}$ aryl, $NR_7R_8$, $OR_7$, $SR_7$, $C_1$–$C_6$ alkyl-C(O)$R_7$, $C_1$–$C_6$ alkyl-C(O)$NR_7R_8$, $C_1$–$C_6$ alkyl-C(O)$OR_7$, $C_1$–$C_6$ alkyl-OC(O)$R_7$, $C_1$–$C_6$ alkyl-$OR_7$, $OC_1$–$C_6$ alkyl-C(O)$R_7$, $OC_1$–$C_6$ alkyl-C(O)$OR_7$, $OC_1$–$C_6$ alkyl-OC(O)$R_7$, O—$C_1$–$C_6$ alkyl-$OR_7$, $OC_1$–$C_6$ alkyl-C(O)$NR_7R_8$, $C_1$–$C_6$ haloalkyl, $OR_{12}$, $C_1$–$C_6$ alkyl-$R_{12}$, O—$C_1$–$C_6$ alkyl-$R_{12}$, C(O)$OR_7$, C(O)$OR_{12}$, C(O)$NR_7R_8$, OC(O)$NR_7R_8$, $NR_7C(O)R_7$, $NR_7C(O)R_{12}$, $NR_7C(O)$—$NR_7R_8$, $NR_7$—($C_1$–$C_6$ alkyl)-C(O)—$NR_7R_8$, $NR_7C(O)OR_7$, $NR_7C(O)OR_{12}$, $NR_7S(O)_n$—$R_1$, $NR_7S(O)_n$—$R_7$ and $NR_7S(O)_n$—$R_{12}$, wherein $R_{12}$ is unsubstituted or substituted $C_6$–$C_{10}$ aryl and n is 1 or 2; and acid and base addition salts thereof.

26. The compound of claim 25 having formula II:

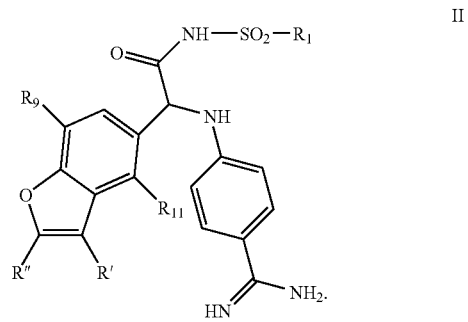

27. The compound of claim 26 having the structure:
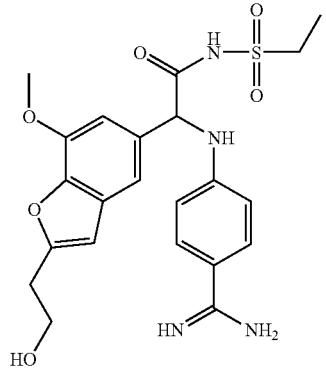
28. The compound of claim 26 having the structure:
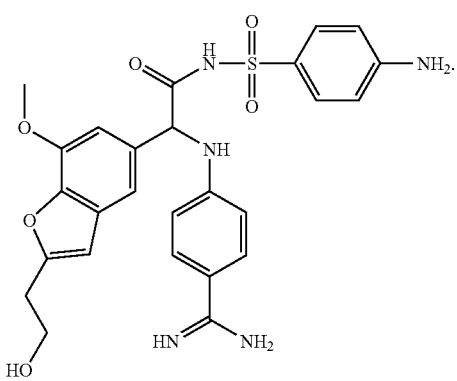
29. The compound of claim 28 selected from:
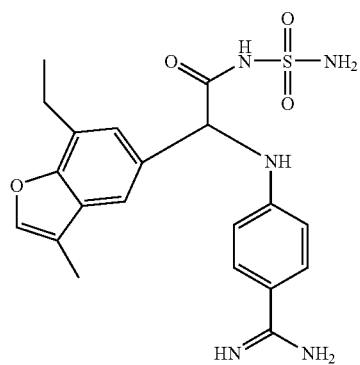
-continued
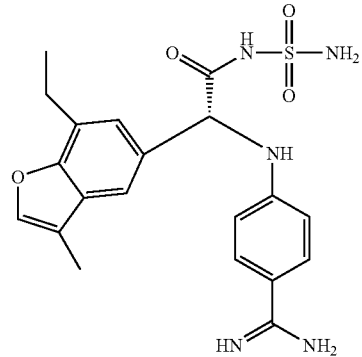
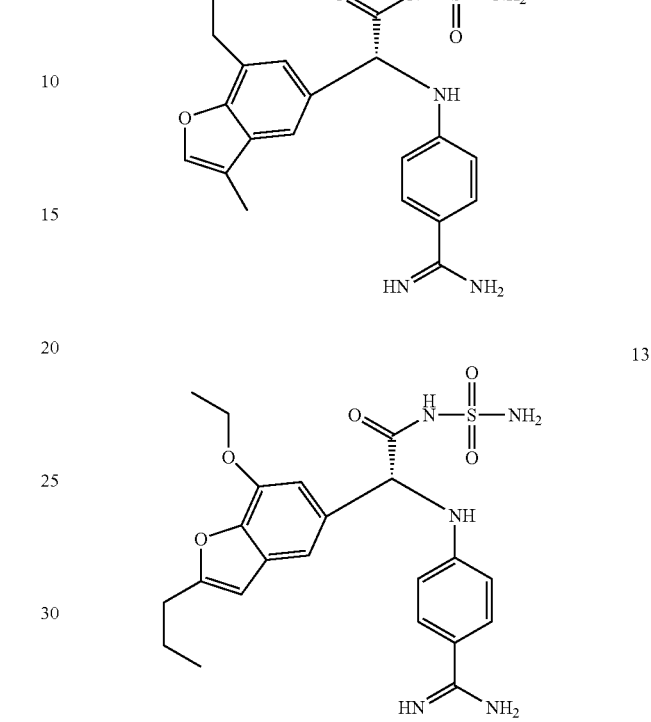
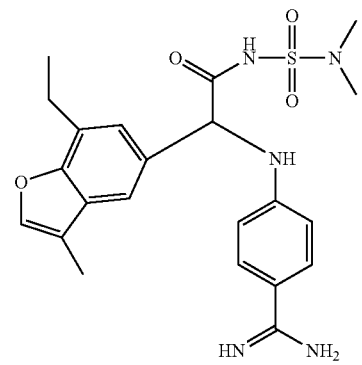
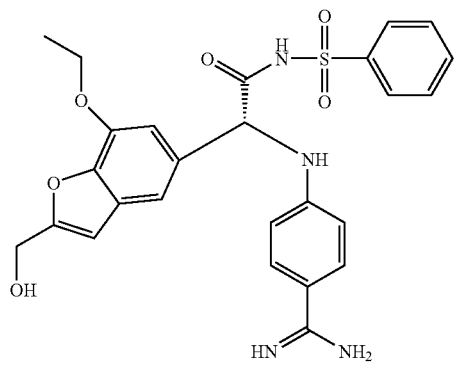

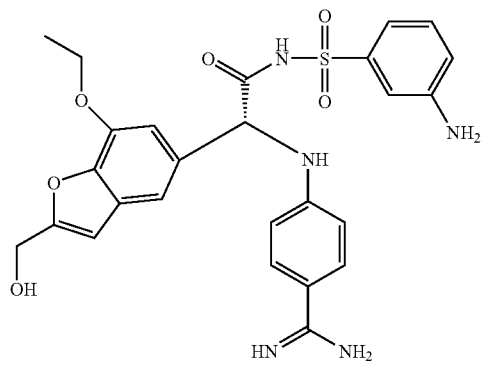

16

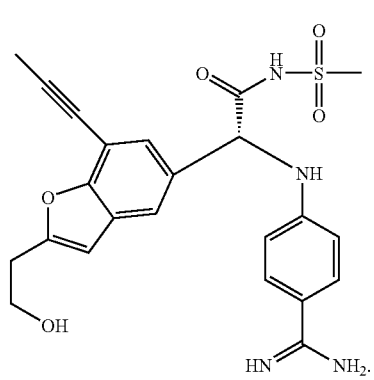

22 and

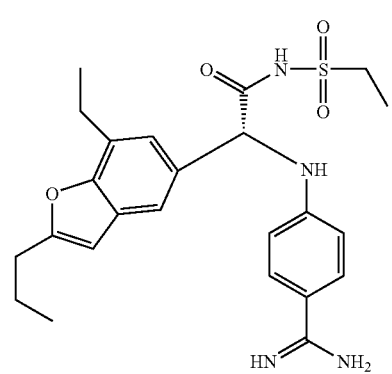

19

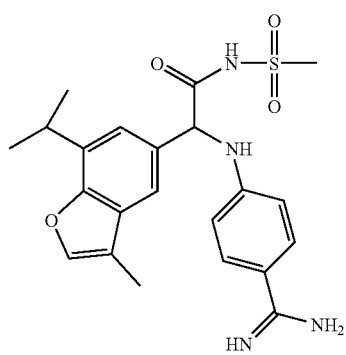

24

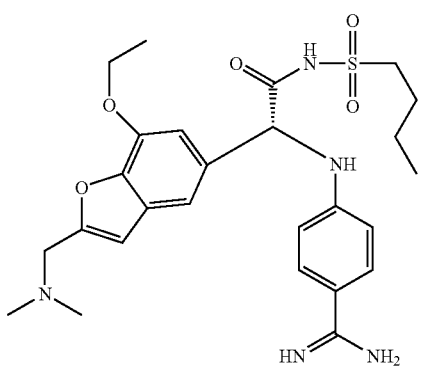

21

30. A pharmaceutical composition comprising an effective amount of the compound of claim 1, or 28 or a pharmaceutically acceptable salt thereof, and a pharmaceutically acceptable diluent, carrier or excipient.

31. The pharmaceutical composition of claim 30 formulated in a unit dosage form.

32. The pharmaceutical composition of claim 30 administered orally.

33. The pharmaceutical composition of claim 30 administered parenterally.

* * * * *